US010165966B2

(12) United States Patent
Banner et al.

(10) Patent No.: US 10,165,966 B2
(45) Date of Patent: Jan. 1, 2019

(54) METHODS AND SYSTEMS FOR MONITORING RESISTANCE AND WORK OF BREATHING FOR VENTILATOR-DEPENDENT PATIENTS

(71) Applicants: University of Florida Research Foundation, Inc., Gainesville, FL (US); Convergent Engineering, Inc., Newberry, FL (US)

(72) Inventors: Michael J. Banner, Alachua, FL (US); Neil Russell Euliano, Gainesville, FL (US); Andrea Gabrielli, Gainesville, FL (US); Nawar Nazar Yousif Al-Rawas, Gainesville, FL (US)

(73) Assignees: University of Florida Research Foundation, Incorporated, Gainesville, FL (US); Convergent Engineering, Inc., Newberry, FL (US)

( * ) Notice: Subject to any disclaimer, the term of this patent is extended or adjusted under 35 U.S.C. 154(b) by 991 days.

(21) Appl. No.: 14/197,486

(22) Filed: Mar. 5, 2014

(65) Prior Publication Data

US 2014/0276173 A1 Sep. 18, 2014

Related U.S. Application Data

(60) Provisional application No. 61/781,623, filed on Mar. 14, 2013.

(51) Int. Cl.
*A61B 5/00* (2006.01)
*A61B 5/085* (2006.01)
(Continued)

(52) U.S. Cl.
CPC .............. *A61B 5/085* (2013.01); *A61B 5/087* (2013.01); *A61B 5/4836* (2013.01);
(Continued)

(58) Field of Classification Search
USPC ...................................... 600/533; 128/204.23
See application file for complete search history.

(56) References Cited

U.S. PATENT DOCUMENTS

| 4,838,259 A | 6/1989 | Gluck et al. |
| 5,261,397 A | 11/1993 | Grunstein |

(Continued)

FOREIGN PATENT DOCUMENTS

| EP | 0 521 515 A1 | 1/1993 |
| WO | WO 01/00265 A1 | 1/2001 |

(Continued)

OTHER PUBLICATIONS

Al-Rawas, Nawar, et al. "Expiratory time constant for determinations of plateau pressure, respiratory system compliance, and total resistance." Critical Care 17.1 (2013): 1.*

(Continued)

*Primary Examiner* — Christian Jang
*Assistant Examiner* — Mitchell E Alter
(74) *Attorney, Agent, or Firm* — Alston & Bird LLP

(57) ABSTRACT

Methods for non-invasively and accurately estimating and monitoring resistance and work of breathing parameters from airway pressure and flow sensors attached to the ventilator-dependent patient using an adaptive mathematical model are provided. These methods are based on calculations using multiple parameters derived from the above-mentioned sensors. The resistance and work of breathing parameters are important for: assessing patient status and diagnosis, appropriately selecting treatment, assessing efficacy of treatment, and properly adjusting ventilatory support.

20 Claims, 19 Drawing Sheets

(51) Int. Cl.
  *A61B 5/087* (2006.01)
  *A61M 16/04* (2006.01)
  *A61M 16/08* (2006.01)
  *A61M 16/00* (2006.01)
  *G06F 19/00* (2018.01)

(52) U.S. Cl.
  CPC .... *A61M 16/0003* (2014.02); *A61M 16/0051* (2013.01); *A61M 16/0069* (2014.02); *A61M 16/026* (2017.08); *A61M 16/0434* (2013.01); *A61M 16/0833* (2014.02); *A61M 16/0858* (2014.02); *A61M 16/0883* (2014.02); *G06F 19/00* (2013.01); *A61M 2016/003* (2013.01); *A61M 2016/0027* (2013.01)

(56) References Cited

U.S. PATENT DOCUMENTS

| | | | |
|---|---|---|---|
| 5,303,698 | A | 4/1994 | Tobia et al. |
| 5,316,009 | A | 5/1994 | Yamada |
| 5,400,777 | A | 3/1995 | Olsson et al. |
| 5,429,123 | A | 7/1995 | Shaffer et al. |
| 5,490,502 | A | 2/1996 | Rapoport et al. |
| 5,682,881 | A | 11/1997 | Winthrop et al. |
| 5,692,497 | A | 12/1997 | Schnitzer et al. |
| 5,752,921 | A | 5/1998 | Orr |
| 5,807,245 | A | 9/1998 | Aldestam et al. |
| 5,876,352 | A | 3/1999 | Weismann |
| 5,887,611 | A | 3/1999 | Lampotang et al. |
| 5,941,841 | A | 8/1999 | Mutch et al. |
| 5,953,713 | A | 9/1999 | Behbehani et al. |
| 6,004,267 | A | 12/1999 | Tewari et al. |
| 6,019,732 | A | 2/2000 | Volgyesi |
| 6,027,498 | A | 2/2000 | Mutch et al. |
| 6,058,322 | A | 5/2000 | Nishikawa et al. |
| 6,068,602 | A | 5/2000 | Tham et al. |
| 6,083,173 | A | 7/2000 | Grant et al. |
| 6,099,481 | A | 8/2000 | Daniels et al. |
| 6,135,105 | A | 10/2000 | Lampotang et al. |
| 6,158,432 | A | 12/2000 | Biondi et al. |
| 6,179,784 | B1 | 1/2001 | Daniels et al. |
| 6,240,920 | B1 | 6/2001 | Strom |
| 6,257,234 | B1 | 7/2001 | Sun |
| 6,290,654 | B1 | 9/2001 | Karakasoglu |
| 6,390,091 | B1 | 5/2002 | Banner et al. |
| 6,439,229 | B1 | 8/2002 | Du et al. |
| 6,450,164 | B1 | 9/2002 | Banner et al. |
| 6,629,934 | B2 | 10/2003 | Mault et al. |
| 7,566,310 | B2 | 7/2009 | Badr et al. |
| 8,728,002 | B2 | 5/2014 | Al-Rawas et al. |
| 2003/0050568 | A1 | 3/2003 | Green et al. |
| 2005/0284469 | A1 | 12/2005 | Tobia et al. |
| 2007/0185406 | A1 | 8/2007 | Goldman |
| 2007/0232951 | A1 | 10/2007 | Euliano et al. |
| 2009/0272382 | A1 | 11/2009 | Euliano et al. |
| 2012/0330177 | A1* | 12/2012 | Al-Rawas .............. A61B 5/091 600/533 |

FOREIGN PATENT DOCUMENTS

| | | |
|---|---|---|
| WO | WO 02/28281 A1 | 4/2002 |
| WO | WO 2011/090716 A2 | 7/2011 |

OTHER PUBLICATIONS

Al-Rawas, Nawar et al., "Real-Time Calculation of Respiratory System Compliance (CRS) and Plateau Pressure (PPLT) During Pressure Support Ventilation (PSV)," *American Journal of Respiratory and Critical Care Medicine*, Poster: Mechanical Ventilation—Thematic Poster Session, 2011, 183:A1693.

Al-Rawas, Nawar et al., "Real-time determination of respiratory system resistance (Rrs) during pressure support ventilation (PSV) using the expiratory time constant ($T_E$)," *ASA/SOCCA 2011 meeting poster*, Sep. 6, 2011.

Al-Rawas, Nawar et al., "Real-Time Measurements of Inspiratory Plateau Pressure (PPLT), Respiratory System Compliance (CRS), and Resistance (RRS) During Ventilatory Support," *Critical Care Medicine*, Poster: Pulmonary—Mechanical Ventilation—1, 2010, 38(12):A344.

Banner, Michael J. "Respiratory muscle loading and the work of breathing," *Journal of Cardiothoracic and Vascular Anesthesia*, 1995, Saunders, Philadelphia, PA, 9(2):192-204.

Banner, Michael J. et al., "Breathing Frequency and Pattern Are Poor Predictors of Work of Breathing in Patients Receiving Pressure Support Ventilation," *Chest*, 1995, 108:1338-1344.

Banner, Michael J. et al., "Power of breathing determined noninvasively with use of an artificial neural network in patients with respiratory failure," *Critical Care Medicine*, 2006, 34(4):1051-1059.

Brunner, Josef X. et al., "Simple method to measure total expiratory time constant based on the passive expiratory flow volume curve," *Critical Care Medicine*, 1995, 23:1117-1122.

Guerin, Claude et al., "Effect of Peep on work of breathing in mechanically ventilated COPD patients," *Intensive Care Medicine*, 2000, 26(9):1207-1214.

Guerin, Claude et al., "Inhaled Bronchodilator Administration During Mechanical Ventilation: How to Optimize It, and for Which Clinical Benefit?" *Journal of Aerosol Medicine and Pulmonary Drug Delivery*, 2008, 21(1):85-95.

Guttmann, J. et al., "Time constant/volume relationship of passive expiration in mechanically ventilated ARDS patients," *European Respiratory Journal*, 1995, 8:114-120.

Henderson, William R. et al., "Pulmonary mechanics during mechanical ventilation," *Respiratory Physiology & Neurobiology*, 2012, 180:162-172.

Hess, D. et al., "Comparison of six methods to calculate airway resistance during mechanical ventilation in adults," *J. Clin. Monit.*, 1993, 9(4):Abstract.

Kirton, Orlando C. et al. "Elevated imposed work of breathing masquerading as ventilator weaning intolerance," *Chest*, 1995, 108(4):1021-1025.

Leon, Mauricio A. et al., "Ventilation Mode Recognition Using Artificial Neural Networks," *Computers and Biomedical Research*, 1997, 30(5):373-378.

Lichtwarck-Aschoff, M. et al., "Good short-term agreement between measured and calculated tracheal pressure," *British Journal of Anaesthesia*, 2003, 91(2):239-48.

Lourens M.S. et al., "Expiratory time constants in mechanically ventilated patients with and without COPD," *Intensive Care Medicine*, 2000, 26(11):1612-1618.

MacIntyre, Neil R. "Weaning from Mechanical Ventilatory Support: Volume-Assisting Intermittent Breaths versus Pressure-Assisting Every Breath," *Respiratory Care*, 1988, 33(2):121-125.

NIH NHLBI ARDS, *Clinical Network Mechanical Ventilation Protocol Summary*, Jul. 2008, accessed from: http://www.ardsnet.org/node/77791.

Rumelhart, David E. et al., "Learning Internal Representations by Error Propagation," *Institute for Cognitive Science*, Sep. 1985, University of California, San Diego, CA, p. 1-49.

Wilder, Nicholas A. et al., "Clinical evaluation of tracheal pressure estimation from the endotracheal tube cuff pressure," *J Clin Monit Comput.*, 1998, 14(1):Abstract.

Gay, P. C. et al., *Evaluation of Bronchodilator Responsiveness in Mechanically Ventilated Patients*, Am. Rev. Respir. Dis. 136:880-885 (1987).

Wilder, N. A. et al., *Evaluation in Animals of a System to Estimate Tracheal Pressure From the Endotracheal Tube Cuff*, Journal of Clinical Monitoring, 12(1): 11-6 (1996).

* cited by examiner

METHODS AND SYSTEMS FOR MONITORING RESISTANCE AND WORK OF BREATHING FOR VENTILATOR-DEPENDENT PATIENTS

CROSS-REFERENCE TO A RELATED APPLICATION

This application claims the benefit of U.S. provisional application Ser. No. 61/781,623, filed Mar. 14, 2013, which is incorporated herein by reference in its entirety.

BACKGROUND OF INVENTION

Mechanical ventilatory support is widely accepted as an effective form of therapy and means for treating patients with respiratory failure. Ventilation is the process of delivering oxygen to and exhaling carbon dioxide from the lungs. When receiving ventilatory support, the patient becomes part of a complex interactive system which is expected to provide adequate ventilation and promote gas exchange to aid in the stabilization and recovery of the patient. Clinical treatment of a ventilated patient often calls for monitoring a patient's breathing to detect an interruption or an irregularity in the breathing pattern, for triggering a ventilator to initiate assisted breathing, and for interrupting the assisted breathing periodically to wean the patient off of the assisted breathing regime, thereby restoring the patient's ability to breathe independently.

A patient whose breathing is being supported by a ventilator typically receives breathing gas through a ventilator conduit. The ventilator conduit generally consists of two flexible conduits, an inhalation conduit and an exhalation conduit, connected to a wye fitting. The free ends of the conduits are attached to the ventilator so that the inhalation conduit receives breathing gas from the ventilator's pneumatic system and the exhalation conduit is attached to an exhalation valve, permitting exhalation to the atmosphere. The wye fitting is typically connected to the patient's breathing attachment, which is oftentimes an endotracheal tube, which conducts breathing gas into the lungs of the patient, and exhaled gas from the lungs of the patient to the exhalation conduit.

In those instances where a patient requires mechanical ventilation due to respiratory failure, a wide variety of mechanical ventilators is available. Most modern ventilators allow the clinician to select and use several modes of inhalation either individually or in combination. These modes can be defined in three broad categories: spontaneous, assisted or mechanically controlled. During spontaneous ventilation without other modes of ventilation, the patient breathes at his own pace, but other interventions may affect other parameters of ventilation including the tidal volume and the baseline pressure within the system. In assisted ventilation, the patient initiates the inhalation by lowering the baseline pressure, and then the ventilator "assists" the patient by completing the breath by the application of positive pressure. During mechanically controlled ventilation, the patient is unable to breathe spontaneously or initiate a breath, and is therefore dependent on the ventilator for every breath.

Regarding intubated patients receiving ventilator support, resistance and work of breathing are measured because these parameters are essential for correct bedside patient assessment and for evaluating the effects of ventilator therapy. Respiratory resistance is the amount of pressure required to deliver a given flow of gas and is expressed in terms of a change in pressure divided by flow. Total respiratory resistance ($R_{TOT}$) is the sum of physiologic airways resistance ($R_{AW}$) and endotracheal tube resistance ($R_{ETT}$) (i.e., $R_{TOT}=R_{AW}+R_{ETT}$). The standard units of resistance are cm H20/L/second.

Bronchodilator therapy is widely used in mechanically ventilated patients with severe asthma and/or chronic obstructive pulmonary disease. Studies have demonstrated that mechanically ventilated patients, including some patients without a previous diagnosis of airway obstruction, have improvement in their expiratory airflow after bronchodilator administration (Gay P. C. et al., "Evaluation of bronchodilator responsiveness in mechanically ventilated patients," *Am. Rev. Respir. Dis.* 136:880-885 (1987)). Previous studies have not been able to distinguish the individual contribution of $R_{AW}$ and $R_{ETT}$ to $R_{TOT}$; however, this information could enable clinicians with new tools to improve the level of care for the patient. For example, increased $R_{TOT}$ secondary to abnormally increased $R_{AW}$ indicates the need for bronchodilator treatment, while increased $R_{TOT}$ as a result of increased $R_{ETT}$ indicates the need to evaluate the patency of the endotracheal tube or to suction it and not administer bronchodilator treatment.

Bronchodilator administration is given to many patients, some of which administration is effective in opening patient airways, decreasing airway resistance and generally making it easier for the patient to breathe. Bronchodilators given in excess may cause unwanted side effects such as nervousness, restlessness, trembling, and dry mouth. Previous inventors have taught that by optimizing bronchodilator administration of the time and duration of application one can reduce the amount of unneeded bronchodilation therapy administered, US 2005/0284469 A1. To date, clinicians do not measure at the patient's bedside either physiologic airway resistance or endotracheal tube resistance because these parameters are not intuitively measurable. Currently, only total respiratory resistance is measured or estimated at the bedside. The conventional method of measuring total respiratory resistance requires a clinician to temporarily interrupt the patient's breathing and apply an end inspiratory pause. The clinician then has to carefully measure pressures and flows and perform calculations by hand. This unwieldy method provides an assessment of $R_{TOT}$ only, and does not account for $R_{AW}$ and $R_{ETT}$. Moreover, this method of determining respiratory resistance is impractical for spontaneously breathing patients, such as those receiving pressure support ventilation (PSV) and intermittent mandatory ventilation (IMV).

In addition, without measuring $R_{AW}$ and $R_{ETT}$, appropriate ventilatory therapy may be compromised and therapeutic resources squandered. Presently, clinicians routinely implement bronchodilator breathing treatments upon increased $R_{TOT}$. Unfortunately, in the inventor's experience, as much as 25% or more of those instances do not require the treatment because $R_{AW}$ is not increased. Rather, $R_{ETT}$ is increased and the proper strategy would have been to evaluate the patency of the endotracheal tube. Thus, at least 25% in resources and monetary savings associated with bronchodilator treatments can be recouped if $R_{AW}$ and $R_{ETT}$ could be monitored for ventilator-dependent patients.

The total work of breathing (work to initiate and sustain a breath, "$WOB_{TOT}$") performed by a patient's inspiratory muscles to inhale while intubated and attached to the ventilator may be divided into two major components: physiologic work of breathing ($WOB_P$) and breathing apparatus (endotracheal tube and ventilator) imposed resistive work of (WOB$_I$). The total work of breathing (i.e., WOB$_{TOT}$=WOB$_P$+WOB$_I$) can be measured and quantified in joules/min.

WOB$_{TOT}$ with WOB$_P$ and WOB$_I$ information are important for identifying physiologic and imposed factors influencing changes in work of breathing or the loads on the inspiratory muscles to spontaneously inhale. For example, increased WOB$_{TOT}$ secondary to abnormally increased WOB$_P$ indicates the need to apply increased ventilatory support to unload the inspiratory muscles.

Conventional methods of measuring work of breathing require a clinician to insert a special esophageal balloon catheter, use special equipment and perform accurate bedside calculations. Specially trained personnel are needed. This is also an unwieldy method that provides limited information as it is an assessment of WOB$_{TOT}$ only and provides no information regarding WOB$_P$ and WOB$_I$.

When patients are evaluated for extubation, work of breathing is assessed. If WOB$_{TOT}$ is abnormally increased, most physicians may conclude the patient should remain intubated. Unfortunately, this does not take into account either WOB$_I$ or WOB$_P$. Where it is determined that WOB$_{TOT}$ is increased due to increased WOB$_I$ and WOB$_P$ is normal, then the patient may be extubated, saving the hospital and patient the cost of a ventilator for another day.

The early generation of mechanical ventilators, prior to the mid-1960s, was designed to support alveolar ventilation and to provide supplemental oxygen for those patients who were unable to breathe due to neuromuscular impairment. Since that time, mechanical ventilators have become more sophisticated and complicated in response to increasing understanding of lung pathophysiology. In an effort to improve a patient's tolerance of mechanical ventilation, assisted or patient-triggered ventilation modes were developed. IMV, a method of ventilatory support that supplements spontaneous ventilation, became possible for adults outside the operating room in the 1970s. Varieties of "alternative" ventilation modes addressing the needs of severely impaired patients continue to be developed.

In recent years, microprocessors have been introduced into modern ventilators. Microprocessor ventilators are typically equipped with sensors that monitor breath-by-breath flow, pressure, and volume, and derive respiratory parameters. Their ability to sense and transduce "accurately," combined with computer technology, makes the interaction between clinician, patient, and ventilator more sophisticated than ever. The prior art microprocessor controlled ventilators suffered from compromised accuracy due to the placement of the sensors required to transduce the data signals. Consequently, complicated algorithms were developed so that the ventilators could "approximate" what was actually occurring within the patient's lungs on a breath-by-breath basis. In effect, the computer controlled prior art ventilators were limited to the precise, and unyielding, nature of the mathematical algorithms that attempted to mimic cause-and-effect in the ventilator support provided to the patient.

U.S. Pat. No. 5,316,009, which is incorporated herein by reference, describes an apparatus for monitoring respiratory muscle activity based on measuring resistance and elastance of the lung and then calculating a value called respiratory muscle pressure (P$_{MUS}$) from the equation:

$$P_{APPLIED} = P_{VENTILATOR} + P_{MUS} = (R_{TOT} \cdot \text{Flow}) + \frac{V_T}{C_{RS}}$$

where C$_{RS}$ is respiratory system compliance and V$_T$ is the tidal volume. A problem with the method taught by the '009 patent is that Pmus is difficult to measure in a spontaneously breathing patient because the parameters R$_{TOT}$ and Crs must be very accurately computed in order for Pmus to correlate with "work". Moreover, R$_{TOT}$ and Crs in a spontaneously breathing patient with ventilator support are very difficult to obtain accurately.

Airway occlusion pressure for 0.1 seconds after breath initiation by a patient (P$_{0.1}$) has also been proposed as an indicator of work of breathing. P$_{0.1}$ can be based on esophageal pressure or airway pressure. An esophageal pressure P$_{0.1}$ is invasive but correlates fairly well with work of breathing. An airway pressure P$_{0.1}$ is non-invasive, but does not correlate nearly as well with work of breathing.

U.S. Pat. No. 5,752,921, which is incorporated herein by reference, describes an apparatus for determining tracheal pressure based on an inflatable cuff located on an endotracheal tube. Unfortunately, this patent provides no description or suggestion regarding the specific component variables of R$_{AW}$, R$_{ETT}$, WOB$_I$ and WOB$_P$ for respiratory resistance and work of breathing, respectively, let alone how one would utilize the measured tracheal pressure to determine these specific component variables. Further, the patent requires the patient be subjected to an end-inspiratory and end-expiratory pause, which is not ideal for patient treatment, to accurately obtain pressure cuff measurements and applies to only one form of ventilatory support, controlled mechanical ventilation. Additionally, this patent does not teach that this method of determining tracheal pressure can be used for spontaneously breathing patients receiving ambient pressure or forms of positive pressure ventilation.

A number of other patents exist for respiratory systems including U.S. Pat. Nos. 6,439,229; 6,390,091; 6,257,234; 6,068,602; 6,027,498, 6,019,732; 5,941,841; 5,887,611; 5,876,352; 5,807,245; and 5,682,881, all of which are incorporated herein by reference.

Accordingly, there is a need in the art for a method and system to noninvasively and automatically monitor resistance and work of breathing, particularly R$_{AW}$, R$_{ETT}$, WOB$_P$ and WOB$_I$, in a ventilator-dependent patient. Furthermore a device to automatically deliver bronchodilator therapy based upon the patient's airway status and/or to monitor the effectiveness of a patient's response receiving bronchodilator therapy would prove to be novel in the art. The present invention is designed to address this need.

BRIEF SUMMARY

The principle object of the invention is to provide methods for automatically and non-invasively estimating resistance, compliance, and work of breathing; and furthermore to provide systems utilizing the estimations to support the optimization of patient ventilation, including ET-tube monitoring, patient airway monitoring, and bronchodilator therapy. In particular, the invention provides methods and systems for predicting (estimating) R$_{AW}$, R$_{ETT}$, WOB$_I$ and WOB$_P$ components for R$_{TOT}$ and WOB$_{TOT}$, respectively.

All of these parameters (R$_{AW}$, R$_{ETT}$, R$_{TOT}$, WOB$_I$, WOB$_P$, and WOB$_{TOT}$) are useful in assessing patient status and the effects of ventilator therapy as well as in determining the most appropriate settings on a ventilator used to support the patient's breathing. For example, measuring patient work of breathing/effort allows for appropriate ventilatory support that avoids inspiratory muscle fatigue and respiratory muscle deconditioning. Measuring imposed patient effort allows for more appropriate ventilatory support by allowing for the imposed effort to be decreased to zero by using pressure support ventilation to simulate natural breathing and is an important extubation criterion. Measuring $R_{AW}$ and $R_{ETT}$ allows for more appropriate bronchodilator treatments, in addition to more accurate monitoring of the patency of the endotracheal tube and the status of the patient's airways.

In one aspect of the invention, the method comprises creating a mathematical model for accurately estimating $R_{TOT}$ and $WOB_{TOT}$, including $R_{AW}$, $R_{ETT}$, $WOB_P$ and $WOB_I$ in real-time (e.g., while a patient is receiving ventilatory treatment), using parameters that are collected non-invasively, such as those collected with standard ventilator devices. Ventilators typically contain airway pressure and airway flow sensors that measure the flow going into and out of the patient, often times including a carbon dioxide sensor and pulse oximeter. With certain ventilatory systems, an endotracheal tube sensor may be used to determine tracheal pressure. Endotracheal tubes typically contain cuffs that are inflated to prevent the tube from falling out of the trachea. It has been discovered that the pressure in this inflated cuff can also be measured to reflect useful, real-time information about changes in pressure in the trachea during inhalation and exhalation for spontaneous positive pressure ventilation. These changes in tracheal pressure are useful for characterizing different aspects of the patient's breathing and/or the patient's interaction with the ventilator. Specifically, the measured tracheal pressure from a cuff can be determined from a patient, without the need for an intermittent pause, to accurately estimate $R_{AW}$, $R_{ETT}$, $R_{TOT}$, $WOB_{TOT}$, $WOB_P$ and $WOB_I$.

In one embodiment of the invention, the endotracheal tube sensor is that described in U.S. Pat. No. 5,752,921; the disclosure of which is herein incorporated by reference.

In one aspect of the invention for estimating $R_{TOT}$, the method comprises creating a mathematical model of the patient's expiratory time constant ($\tau_E$) of the respiratory system by using predetermined parameters that are collected non-invasively as taught by International PCT Application Publication No. WO 2011/090716, which is incorporated herein by reference in its entirety. In one embodiment, real time respiratory resistance or $R_{TOT}$ is accurately and continuously estimated using $\tau_E$ from passive deflation of the lungs during all modes of breathing, preferably during spontaneous or assisted ventilation. More preferably, real time $R_{TOT}$ is accurately and continuously estimated using $\tau_E$ from passive deflation of the lungs during pressure regulated breathing, without the step of imposing an end-inspiratory and/or end-expiratory pause (e.g., without interruption of patient breathing).

The direct measurement of $R_{AW}$ and $R_{ETT}$ of a patient are difficult and often require special and invasive equipment. To address this deficiency, the subject invention provides accurate predicted (estimated) measurements for parameters $R_{ETT}$ and $R_{AW}$, where the estimated measurement of $R_{TOT}$ is determined by employing the expiratory time constant during passive exhalation as described above. Estimated $R_{ETT}$ is then determined by measuring the difference in breathing circuit wye (Y)-piece pressure and the pressure at distal end of the endotracheal tube and dividing the difference by peak inspiratory flow rate. The pressure at the distal end of the endotracheal tube may be determined using a variety of systems and methods, including using an endotracheal tube pressure sensing device. With estimated, accurate measurements for $R_{TOT}$ and $R_{ETT}$, an accurate estimate for $R_{AW}$ can then be determined by the equation: $R_{AW}=R_{TOT}-R_{ETT}$.

Currently, because $R_{AW}$ and $R_{ETT}$ values are difficult to measure, only $R_{TOT}$ can be determined. The conventional method for determining $R_{TOT}$ is to temporarily interrupt the breathing pattern on the ventilator and apply an end-inspiratory pause. During the pause, measurements of pressure and flow rate are obtained, used for determining $R_{TOT}$. Bronchodilator treatment is commonly administered to the patient on the ventilator when an increase in $R_{TOT}$ is measured. However, bronchodilator therapy is only appropriate when there is an increase in $R_{AW}$; it is inappropriate or not required when $R_{AW}$ and $R_{ETT}$ is too high. Rather, an increase in $R_{ETT}$ is an indication there is a partial obstruction of the endotracheal tube, either due to clogging of biomaterial within the endotracheal tube (i.e., patency of the endotracheal tube) or due to a kink in the endotracheal tube itself. Therefore, a further objective of the invention is to provide an open loop method and corresponding system for determining and monitoring changes in $R_{ETT}$ and $R_{AW}$ and advising the clinician of any such changes and with suggestions regarding necessary actions to address these changes so that $R_{ETT}$ and/or $R_{AW}$ are maintained within a desired range selected by the operating clinician.

An open loop method of monitoring resistance and bronchodilator treatment could determine whether bronchodilators are likely to be effective in improving the patient's ability to breathe before bronchodilators are administered. Similarly, the method will provide continuous monitoring of the effectiveness of the bronchodilators over time allowing bronchodilator treatment to be titrated or removed when no longer necessary or effective. In addition to supporting the administration of bronchodilators, the method also monitors the endotracheal tube patency and can therefore provide advice on when the endotracheal tube requires suctioning or cleaning or when it may be occluded or kinked.

A further object of the invention is to provide a closed loop method and corresponding system for continuously monitoring $R_{TOT}$ and $R_{AW}$ in patient on a ventilator, preferably on spontaneous or assisted ventilation, and, upon indication of an increase in $R_{AW}$, automatically providing an appropriate bronchodilator treatment to the patient to decrease $R_{AW}$ so that it is maintained with the selected predetermined $R_{AW}$ range.

$WOB_{TOT}$ can be estimated using any known mathematical models such as with an artificial neural network or Pmus as described above. In a preferred embodiment, $WOB_{TOT}$ is determined by a method using an artificial neural network. $WOB_I$ is determined by integrating the change in pressure at the distal end of the endotracheal tube (as calculated in accordance with the subject invention for use in determining $R_{ETT}$) with the change in volume. $WOB_P$ is determined by the equation: $WOB_P=WOB_{TOT}-WOB_I$. With appropriate pressure and flow sensors placed in the ventilator breathing circuit and software to automatically perform calculations, $R_{TOT}$ and $WOB_{TOT}$ and their component parts are determined.

According to the subject invention, the ability to determine the component parts ($WOB_P$ and $WOB_I$) of $WOB_{TOT}$ enables the clinician to more appropriately manage the patient's respiratory muscles. As indicated above, $WOB_I$ is representative of the imposed work of breathing that comes from the ventilator breathing tube circuitry and endotracheal tube. Having the ability to ascertain $WOB_I$ enables the clinician to accurately "titrate" $WOB_P$ using pressure support ventilation (PSV), inspiration positive airway pressure (IPAP), bilevel positive airway pressure (BIPAP), or any other ventilatory method. In certain instances, the ability to ascertain $WOB_I$ and $WOB_P$ enables the clinician to more accurately determine whether a patient should be extubated and removed from ventilatory support.

A further objective of the invention is to provide an open loop method and corresponding system for determining and monitoring changes in $WOB_P$ and $WOB_I$ in a patient on a ventilator, preferably on spontaneous or assisted ventilation, and advising the clinician of any such changes and with suggestions regarding necessary actions to address these changes so that $WOB_P$ and/or $WOB_I$ are maintained within a desired range selected by the operating clinician.

A further object of the invention is to provide a closed loop method and corresponding system for continuously monitoring $WOB_P$ and $WOB_I$ in a patient on a ventilator, preferably on spontaneous or assisted ventilation, and, upon indication of an increase in $WOB_P$ with no change in $WOB_I$, automatically applying increased ventilatory support to the patient to unload the inspiratory muscles so that $WOB_{TOT}$ is maintained within a predetermined $WOB_{TOT}$ range. Should there be an indication of an increase in $WOB_I$ where there is no change in $WOB_P$, automatically decreasing ventilator support in preparation for extubation of the patient.

The methods described herein may use a linear combination of parameters or a nonlinear combination of parameters, including but not limited to a neural network, fuzzy logic, mixture of experts, or polynomial model. Moreover, multiple different models can be used to estimate the pulmonary mechanics of different subsets of patients. These subsets can be determined by various means, including but not limited to patient condition (pathophysiology), patient physiologic parameters (i.e., inspiratory flow rate, airway resistance, tidal volume, etc.), or other parameters, such as ventilator parameters (i.e., positive end-expiratory pressure or PEEP, patient airway inspiratory pressure, etc.)

This invention applies to the monitoring of patients with respiratory failure attached to life-support ventilators. It could be applied to respiratory monitors, incorporated into a life-support ventilator, or used as an alternative monitoring device. Systems of the invention can be used in an intensive care unit, an operating room or other appropriate venues.

In the aforementioned methods, a neural network is trained by clinical testing of a test population of patients to obtain teaching data, the teaching data which includes the above-noted input information. The teaching data are provided to the neural network, whereby the neural network is trained to provide output variables corresponding to accurate estimates of $R_{TOT}$, $R_{ETT}$, $R_{AW}$, $WOB_P$, $WOB_I$, and $WOB_{TOT}$.

The invention can be implemented in numerous ways, including as a system (including a computer processing or database system), a method (including a computerized method of collecting and processing input data and a method for evaluating such data to provide an output(s)), an apparatus, a computer readable medium, a computer program product, or a data structure tangibly fixed in a computer readable memory. Several embodiments of the invention are discussed below.

As a system, an embodiment of the invention includes a processor unit having input and output devices. The processor unit operates to receive input parameters, process the input and provide an output corresponding to resistance and work of breathing information (e.g., estimated $R_{TOT}$, $R_{ETT}$, $R_{AW}$, $WOB_P$, $WOB_I$, and $WOB_{TOT}$ variables).

In an embodiment, this output can be then used to control external or associated devices, such as a ventilator. The processing of the data can be accomplished by various means such as microcontrollers, neural networks, parallel distributed processing systems, neuromorphic systems, or the like.

As a method of accurately calculating in real time estimates of patient's $R_{TOT}$, $R_{ETT}$, $R_{AW}$, $WOB_P$, $WOB_I$, and $WOB_{TOT}$, the subject invention includes processing predetermined input variables (parameters) using the formulas described herein, preferably through the use of a computer readable media program containing program instructions, a processing system, or a neural network.

As a computer readable medium containing program instructions, an embodiment of the invention includes: computer readable code devices for receiving input variables, processing the input, and providing an output indicative of $R_{TOT}$, $R_{ETT}$, $R_{AW}$, $WOB_P$, $WOB_I$, and $WOB_{TOT}$. In a preferred embodiment, processing comprises utilizing a neural network. The method may further include controlling a ventilator in response to the output obtained.

The methods of the present invention may be implemented as a computer program product with a computer-readable medium having code thereon. The program product includes a program and a signal bearing medium bearing the program.

As an apparatus, the present invention may include at least one processor, a memory coupled to the processor, and a program residing in the memory which implements the methods of the present invention.

The aforementioned methods of determining $R_{TOT}$ and $WOB_{TOT}$ and their component parts are automatic and require no clinician work, are simpler than conventional methods, and provide diagnostic information that heretofore has never been available, e.g., accurate estimates for $R_{AW}$ and $WOB_P$.

Other aspects and advantages of the invention will become apparent from the following detailed description taken in conjunction with the accompanying drawings, illustrating, by way of example, the principles of the invention.

All patents, patent applications, provisional applications, and publications referred to or cited herein, or from which a claim for benefit of priority has been made, are incorporated herein by reference in their entirety to the extent they are not inconsistent with the explicit teachings of this specification.

DETAILED DISCLOSURE

Figure 1:
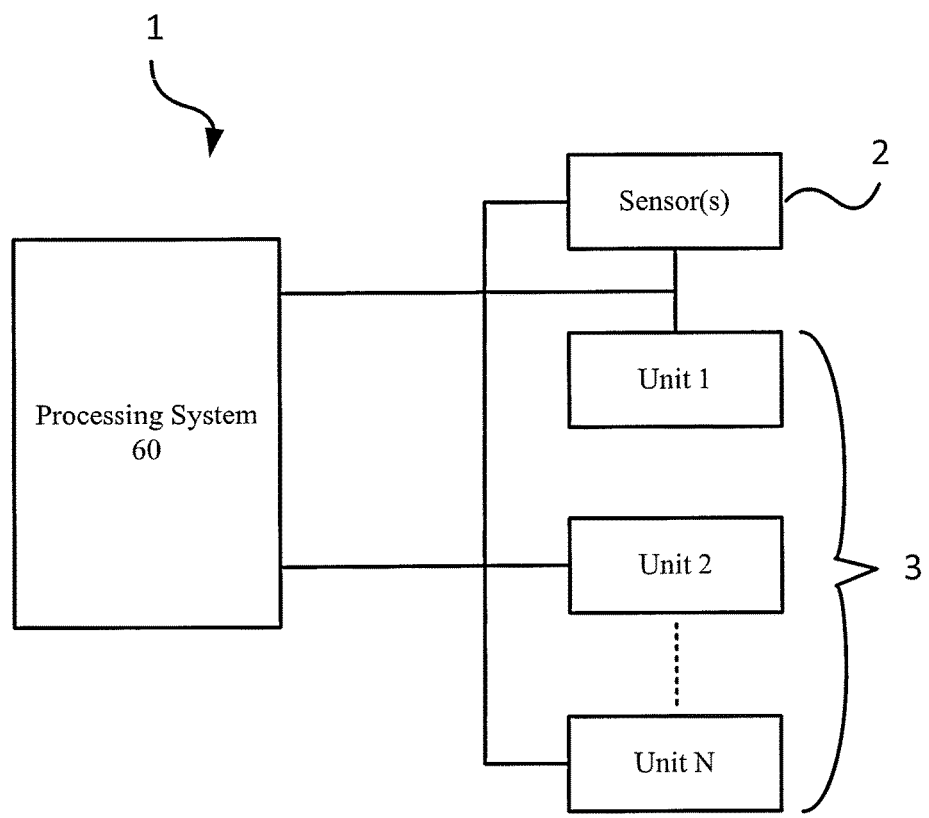
FIG. 1 is a functional block drawing of a ventilation parameter monitoring and/or estimating system embedded on a processing system, in accordance with an exemplary embodiment of the present invention.

Currently, $R_{TOT}$ is obtained in patients during positive pressure inflation by measuring lung pressure during an end-inspiratory pause (EIP, i.e., a pause for at least 0.5 seconds). Unfortunately, there are several disadvantages to performing an EIP, including patient discomfort, requirement for clinician input and careful monitoring, imprecise measurements due to patient interference, patient-ventilator dyssynchrony, inability to be applied continuously, and inability to perform EIP with certain forms of ventilation. Moreover, such methods do not adequately provide estimates for $R_{AW}$ and $R_{ETT}$. To address these deficiencies, the subject invention provides systems and methods for accurately calculating estimated values for $R_{TOT}$, while obviating the need for an EIP and/or an end-expiratory pause. The result is continuous, real time estimates of $R_{TOT}$, $R_{AW}$, and $R_{ETT}$ that are useful in monitoring breath to breath lung function and the effect of therapeutic interventions.

According to the subject invention, the method for estimating, accurately and in real time, $R_{TOT}$, $R_{AW}$ and $R_{ETT}$ for patients receiving ventilation, or any device that interfaces with pulmonary mechanics, involves the following steps: (a) receiving patient respiratory data, including tracheal pressure data, which may be obtained from an intra-tracheal pressure sensing apparatus, a cuff pressure system, or similar tracheal pressure estimation; (b) calculating respiratory parameters from the patient's respiratory data; (c) inputting the tracheal pressure data and necessary respiratory parameters into a mathematical model for determining $R_{ETT}$ and $R_{TOT}$; (d) inputting the $R_{TOT}$ and $R_{ETT}$ into a mathematical model for determining $R_{AW}$ and (e) providing at least one output variable from the mathematical models corresponding to $R_{TOT}$, $R_{AW}$ and $R_{ETT}$. Preferably, the subject invention provides a method for non-invasively estimating, accurately and in real time, $R_{TOT}$, $R_{AW}$ and $R_{ETT}$ for patients receiving spontaneous and/or assisted ventilation without the need for interruption of patient breathing (e.g., an end-inspiratory pause and/or an end-expiratory pause).

According to the subject invention, a patient is an intubated patient on a ventilator or any device that interfaces with pulmonary mechanics. An "invasive" device would include a catheter or balloon or other device that would be used in addition to the established breathing circuit of an intubated patient. "Non-invasive," as defined herein, means absence of an invasive device.

In one embodiment, the tracheal pressure data is applied to a mathematical model for determining $R_{ETT}$. In an alternate embodiment, the respiratory parameters are applied to a mathematical model for determining $R_{TOT}$. The $R_{TOT}$ may be calculated using various conventional models (Scanlan et al, *Egan's Fundamentals of Respiratory Care*, 5th Ed., 1990 The C.V. Mosby Company). For example, $R_{TOT}$ may be determined using a least-squares method, plateau pressure, etc. (Hess and Tabor, "Comparison of six methods to calculate airway resistance during mechanical ventilation in adults," *J Clin Monit.* 1993 September; 9(4):275-82). Preferably, an estimate of $\tau_E$ is calculated from the respiratory parameters and inputted into the mathematical model for determining $R_{TOT}$. More preferably, the estimate of $\tau_E$ is calculated in accordance with that disclosed by International PCT Application Publication No. WO 2011/090716.

Respiratory data can be measured using sensors on a ventilator system, respiratory monitor, or dedicated sensor subsystem. Such respiratory data include, but are not limited to: airway pressure, airway flow, airway volume, exhaled carbon dioxide, and pulse oximeter plethysmogram. Respiratory parameters calculated from the respiratory data, such as via a processor module in a ventilator system, include but are not limited to: tidal volume, breathing frequency, peak inspiratory pressure (PIP), peak inspiratory flow rate (PIFR), inspiratory time, expiratory time, inhalation-to-exhalation time ratio (I:E), occlusion pressure at 0.1 seconds after breath initiation trigger time ($P_{0.1}$), trigger depth PEEP, Pplt, $PetCO_2$, and $VCO_2$.

The following are preferred embodiments of the methods for measuring $R_{TOT}$, $R_{ETT}$, $R_{AW}$, $WOB_{TOT}$, $WOB_1$ and $WOB_P$. To ascertain $R_{AW}$, tracheal pressure must be determined. Tracheal pressure may be determined by use of a tracheal pressure catheter inserted into the endotracheal tube, pressure port built into the distal end of the endotracheal tube, or similar method. Preferably tracheal pressure can be determined using a tracheal pressure sensing device. In one embodiment, the tracheal pressure sensing device is that disclosed in U.S. Pat. No. 5,752,921.

In certain embodiments, the relationship between the tracheal pressure sensing device and airway pressure measured at the start and end of each breath (e.g., where the air flow and airway pressure are zero) is used to calibrate the pressure sensing device and allow determination of tracheal airway pressure (see, for example, Wilder N A et al. "Evaluation in animals of a system to estimate tracheal pressure from the endotracheal tube cuff," *J Clin Monit*, 12(1):11-6 (1996)). In other embodiments, the following equation may be used to calculate tracheal airway pressure from the pressure sensed ($P_{CUFF}$) by the tracheal pressure sensing device:

$$P_{TRACH} = m \cdot P_{CUFF} - b$$

where tracheal pressure is a linear function of cuff pressure and m is the scale factor on the cuff pressure that best approximates the tracheal pressure and b is the bias offset of pressure.

Variables m and b can be calculated as described above where airway pressure and tracheal pressure are equal (e.g., with zero flow). In this case, $P_{TRACH}$ is substituted with $P_{AW}$ and the m and b parameters are identified such that $P_{CUFF}$ best converts to $P_{AW}$ at points of zero flow. This can be performed using adaptive methods, such as least square methods or gradient descent, or conventional analytical methods such as regression analysis or using two different points and estimating the best line between them.

When the tracheal pressure rises significantly above the cuff pressure, the pressure in the cuff is dominated by the tracheal pressure and the two become roughly equivalent. At this point, the cuff pressure is a perfect predictor of tracheal pressure (e.g. m=1 and b=0). The transition between the relationship defined above where m<>1 and b<>0 and the case where m=1 and b=0 typically occurs relatively quickly and can be determined by a similar change in the relationship between Paw and Pcuff. When solving for the parameters of the tracheal pressure equation above, it is important to use only those regions of the curve where the original linear relationship exists. With control of the cuff pressure, changing the cuff pressure may allow for easier modeling of the tracheal/cuff pressure equation. For example, the cuff pressure can be manipulated to ensure the point where the transition occurs is above or below the range of standard operating points, therefore allowing for accurate determination with a single equation of the tracheal pressure. Other uses of these dual relationships or the parameters at the transition may also be helpful in accurately modeling the system.

$R_{ETT}$ can then be calculated by subtracting tracheal airway pressure ($P_{TRACH}$) from pressure measured at the Y-piece (also referred to herein as tracheal pressure or $P_Y$) divided by flow rate (e.g., $R_{ETT}=(P_Y-P_{TRACH})$/flow). In a preferred embodiment that simplifies the calculations when the peak inspiratory flow rate (PIFR) occurs at the end of the breath, the pressure measured at the Y-piece is PIP, the flow rate is the PIFR, and $P_{TRACH}$ is measured at the end of the inhalation, where the equation for $R_{ETT}$ is as follows:

$$R_{ETT} = \frac{PIP - P_{TRACH}}{PIFR}.$$

In other embodiments, particularly where zero air flow and/or airway pressure may not exist or are very transient (such as in spontaneous or assisted breathing modes), a least squares method can be implemented to determine $R_{ETT}$, as follows:
where the following two equations are taken into consideration $$P_{TRACH} = m \cdot P_{CUFF} - b, \text{ and} \quad (1)$$

Tracheal Pressure equation: $P_Y = R_{ETT}*f + K*f^2 + P_{TRACH}.$ (2)

and where tracheal pressure is a linear function of cuff pressure, m is the scale factor on the cuff pressure that best approximates the tracheal pressure, b is the bias offset of pressure, f is the flow at the Y-piece, and K is a scale factor on the square of frequency.

Then, with these equations (1) and (2), the least squares analysis can be performed using airway pressure and flow along with $P_{CUFF}$, where all of the parameters above are derived with $$P_Y = R_{ETT}*f + K*f^2 + m*P_{CUFF} - b.$$

The least-squares fitting method assumes a specific model for the respiratory system, which is common in the respiratory mechanics literature (i.e., Henderson and Sheel, "Pulmonary mechanics during mechanical ventilation," *Respiratory Physiology & Neurobiology*, 180:162-172 (2012), the entirety of which is incorporated herein by reference), and fits the waveform data to that model. It is applied during inhalation, exhalation, or over the whole breath cycle. It uses many of the data points in the breath cycle and tends to be a more robust method than previous methods for resistance which rely on the difference between two points in the breathing cycle. By using many data points from breaths, least squares can be used to fit the model of the equation above, where $P_Y$, f, f^2 and $P_{CUFF}$ are known and $R_{ETT}$, k, m and b are unknown. Least squares method adaptively creates a best fit model of the unknowns to match the equation using the known values (e.g., given the least squares algorithm measured values for $P_Y$, f, f^2 and $P_{OUT}$, best fit values for $R_{ETT}$, k, m and b are determined).

In one embodiment, to determine $R_{TOT}$, an estimate of $\tau_E$ can be used. $\tau_E$ can be was estimated in accordance with methods described in U.S. patent application Ser. No. 13/260,467, which is incorporated herein in its entirety. Specifically, an accurate, modified estimate of $\tau_E$ is achieved by averaging the exhalation waveform slope from 0.1 to 0.5 seconds after the beginning of exhalation. The first part of exhalation (between 0 and 0.1 sec) is excluded to reduce possible interference from the ventilator's exhalation valve during initial opening as well as residual patient effort. The end of exhalation (beyond 0.5 sec) is excluded to address issues attributable to end exhalation as described above.

To determine $R_{TOT}$, $\Sigma_E$ is first estimated and then the following equation is used:

$$R_{TOT} = \frac{PIP - PEEP}{\frac{\text{Tidal volume}}{\tau_E} + PIFR}$$

$$R_{TOT} = \frac{PAW - PEEP}{\frac{\text{Volume}}{\tau_E} + f}.$$

With both $R_{ETT}$ and $R_{TOT}$, $R_{AW}$ can be calculated using the following equation:

$$R_{AW} = R_{TOT} - R_{ETT}.$$

$WOB_{TOT}$/min or power of breathing consists of work of breathing imposed by the apparatus per minute ($WOB_I$/min) and physiologic work of breathing per minute ($WOB_P$/min). $P_{Trach}$ is needed for determinations of endotracheal tube resistance and $WOB_I$/min. Tracheal airway pressure may be determined as described herein using a tracheal pressure sensing apparatus. $WOB_I$ is estimated as:

$$WOB_I = \int P_{Trach} \cdot V_T$$

where $V_T$ is measured tidal volume that is calculated from data from the flow sensor over time.

$WOB_I$ includes flow resistive work caused by the ventilator circuitry, valves, and response time, plus the endotracheal tube. $WOB_P$/min or physiologic power of breathing, is defined as the part of the total work of breathing done by the patient, i.e. the difference between the $WOB_{TOT}$/min and $WOB_I$/min is $WOB_P$/minute.

In certain embodiments, the mathematical models used to determine the desired $WOB_{TOT}$ is determined by a neural network. The neural network can be trained to include clinical testing of a population of subjects using monitored pressure and flow data as clinical data input to the neural network.

The estimated resistance and work of breathing values determined in accordance with the methodologies described herein are particularly useful in enabling appropriate ventilatory support on any device that interfaces with patient pulmonary mechanics. Contemplated devices include, but are not limited to, ventilators, respiratory monitors, multi-function physiologic monitors, pulmonary function machines, sleep apnea systems, hyperbaric devices, custom stand-alone devices and the like. Contemplated ventilators include those that accomplish any one or more of the following modes of ventilation: volume-cycled ventilation; assist-control ventilation (A/C); synchronized intermittent mandatory ventilation (SIMV); pressure-cycled ventilation; pressure support ventilation (PSV); pressure control ventilation (PCV); volume control plus (VC+), noninvasive positive pressure ventilation (NIPPV); and continuous positive airway pressure (CPAP) or bilevel positive airway pressure (BIPAP). Preferably, the estimated resistance and work of breathing values determined in accordance with the methodologies described herein are derived from patients on either assisted or spontaneous ventilation.

In one embodiment of the invention, continuous, real time estimates of $R_{TOT}$, $R_{AW}$, $R_{ETT}$, $WOB_{TOT}$, $WOB_P$ and $WOB_I$ are determined in order to monitor patient status and/or to assess intervention efficacy. For example, continuous accurate knowledge of patient $WOB_{TOT}$, $WOB_P$ and $WOB_I$ is particularly useful in establishing more accurate ventilator settings for the patient. Continuous and accurate knowledge of patient $R_{TOT}$, $R_{AW}$ and $R_{ETT}$ during application of pharmaceuticals is particularly useful in assessing therapeutic efficacy and in determining proper dosage. In addition, the real-time data from this invention could be used to determine partial endotracheal tube obstructions adversely affecting a patient's ventilation. For instance, the invention can be utilized to determine when an endotracheal tube requires suctioning to remove mucus or other obstructions, or may determine when the endotracheal tube may be kinked.

In an embodiment, the model, such as a neural network, is pretrained with clinical data and the input parameters can be collected non-invasively with a standard respiratory monitor or ventilator. The neural network is trained to predict the physiologic and imposed pulmonary mechanics using the non-invasively acquired parameters described above (although invasive parameters may be added to the system, if desired.) Once a model having a desired degree of predictability has been achieved and verified, the network output, such as actual resistance and work of breathing variables may be used as an accurate predictor of resistance and work of breathing variables.

In accordance with an exemplary embodiment of the present invention, a hierarchical architecture for automatically and non-invasively monitoring and estimating ventilation parameters (e.g., resistance, compliance and work of breathing) to support optimization of patient ventilation is provided. This system comprises an operational support system comprising at least one ventilation parameter manager and an optimization decision support module.

In one embodiment of the invention, each manager corresponds to a ventilation parameter of the patient. Preferably, there is at least a resistance parameter manager and a work of breathing manager. Each of the managers is preferably configured to obtain the signal outputs from at least one sensor and obtain results from algorithms that estimate ventilation parameters.

An optimization decision support module is preferably coupled to at least one ventilation parameter manager. The decision support module is configured to receive the manager outputs and provide a decision support output for optimizing patient ventilation based at least in part on the manager outputs. Preferably, the decision support module output provides directions to the user on recommended action based on monitored/estimated patient resistance and work of breathing.

FIG. 1 is a functional block drawing of a ventilation parameter estimating/monitoring system 1, in accordance with an exemplary embodiment of the present invention. In the depicted embodiment, the system 1 includes one or more sensors 2, a processing system 60 and a plurality of additional units 3. However, this may vary in other embodiments.

The one or more sensors 2 are preferably used on a patient. The sensors 2 preferably at least facilitate generation of data pertaining to ventilation parameters. Contemplated sensors include, but are not limited to: pressure sensors (e.g., pressure cuff) and flow sensors. The sensors 2 are preferably coupled to the processing system 60 and the additional units 3. However, this may vary in other embodiments.

The additional units 3 are coupled to the processing system 60 and/or are coupled to one another, for example as depicted in FIG. 1. The additional units 3 may comprise any number of different types of systems, devices, and/or units. For example, in certain embodiments, the additional units 3 may comprise one or more additional computer systems and/or components thereof, one or more sensors, and/or one or more transmitters and/or receiver for transmitting, exchanging, and/or receiving information from non-depicted internal and/or external sources pertaining to patient ventilation. In certain embodiments, the additional unit 3 may be a bronchodilator therapy device, a respiratory monitor, and/or a ventilator.

Figure 2:
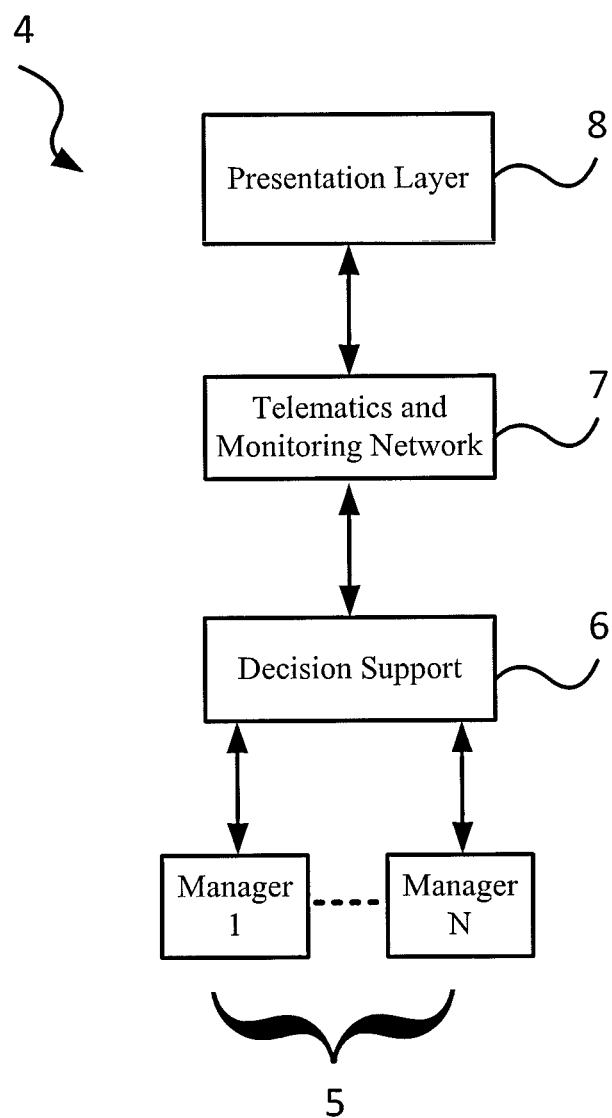
FIG. 2 is a functional block diagram of an operational support system for a ventilation parameter monitoring and/or estimating system, or a program, program product or computer system thereof, that can be used in connection with the processing system of FIG. 1 and/or a program stored in memory thereof.

FIG. 2 is a functional block diagram of an operational support system or architecture 4 and accompanying architecture for a system for monitoring/estimating ventilation parameters, or a program, program product or processing system thereof, such as that depicted in FIG. 1. The operational support system 4 may also be implemented in connection with other devices (e.g., devices configured to implement the system such as a smartphone (mobile phone built on a mobile operating system) or a tablet computer (a one-piece mobile computer)), systems, and/or units in various other embodiments.

As depicted in FIG. 2, the operational support system or architecture 4 comprises an operational support module comprising at least one manager 5, a decision support module 6, a telematics and monitoring network 7 and a presentation layer 8. Each of the managers 5 pertains to a particular ventilation parameter to be estimated and/or monitored. For example, in one embodiment, a resistance manager and a work of breathing manager is provided for estimating and/or monitoring a patient's resistance and work of breathing. It will be appreciated that in other embodiments, various other managers may be utilized for various different ventilation parameters.

Each manager 5 is configured to at least facilitate generating, and is preferably configured to generate, manager output pertaining to a ventilation parameter. In certain embodiments, each manager 5 is configured to conduct analysis on output signals from one or more sensors 2 and/or the additional units 3 of FIG. 1, and/or from one or more other, non-depicted sources within or external to the patient, to thereby generate manager output for use in support in decision-making regarding optimizing patient ventilation.

Preferably, each manager 5 comprises an algorithm or set of algorithms (such as those described herein) that process data, including sensor(s) 2 output data and/or other forms of data, to generate manager output, such as a quantitative estimate for resistance and work of breathing variables. Each manager may include one or more specific methods in addition to the algorithm(s). The methods can be based on techniques such as neural networks, principal component analysis, techniques based on fault tree analysis, document to knowledge capture, model residuals, built-in tests, and data driven techniques. According to the subject application, as new algorithms are developed, they can be added to the system architecture with low risk to the remaining system.

The decision support module 6 is coupled to each manager 5, and receives the manager's output therefrom. In addition, the decision support module 6 performs analysis on the manager 5 output, and generates decision support output. In one embodiment, the decision support output is transmitted to the telematics and monitoring network 7, which in turn transmits the decision support output to the presentation layer 8. It will be appreciated that the telematics and monitoring network 7 may comprise a computer network and/or one or more various other types of diagnostic networks and/or other networks to perform this function.

Ultimately, a user can view the decision support output via the presentation layer 8 and make various decisions pertaining to optimizing patient ventilation. The presentation layer 8 (e.g., displays or user interfaces) is configured to present decision support output for a user of the subject system. In certain embodiments, the decision support output is transmitted to the telematics and monitoring network 7, which in turn automatically implements appropriate action(s) for optimizing patient ventilation.

Figure 3A:
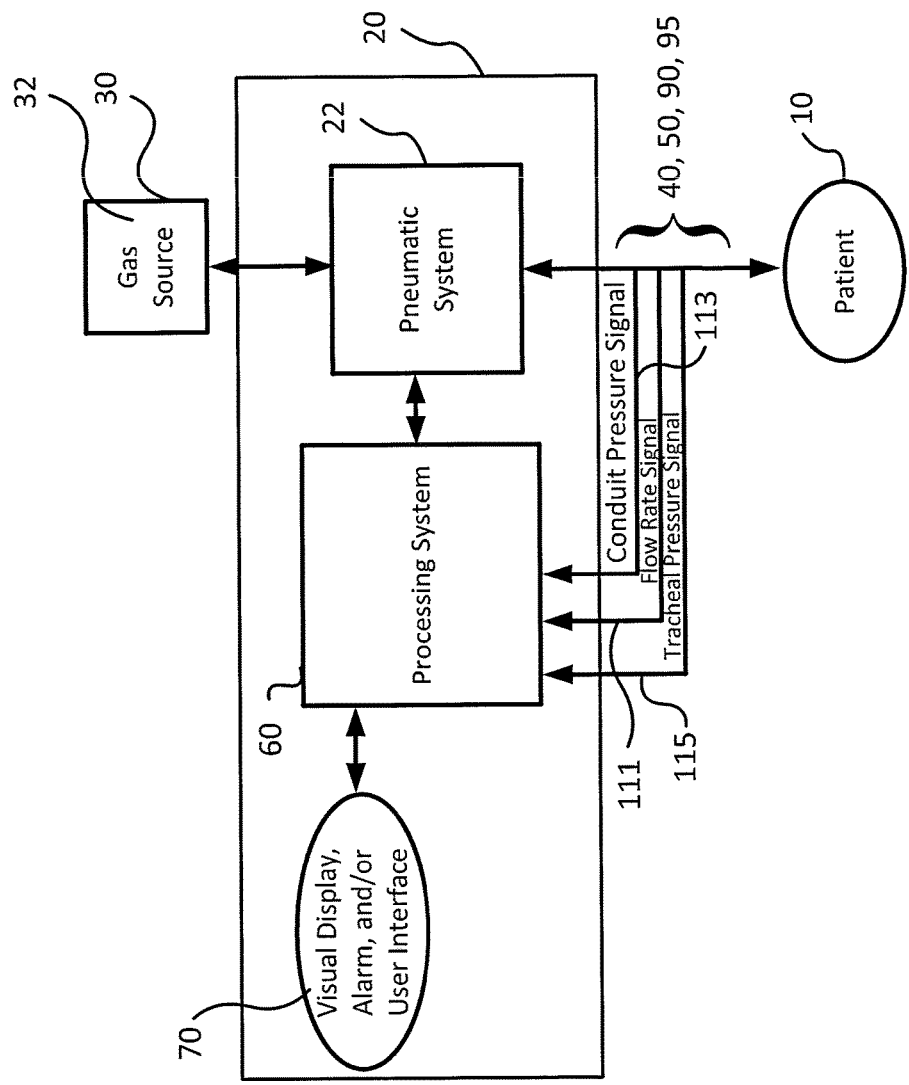
FIG. 3A is a block diagram of a medical ventilator according to one embodiment of the present invention.
Figure 3B:
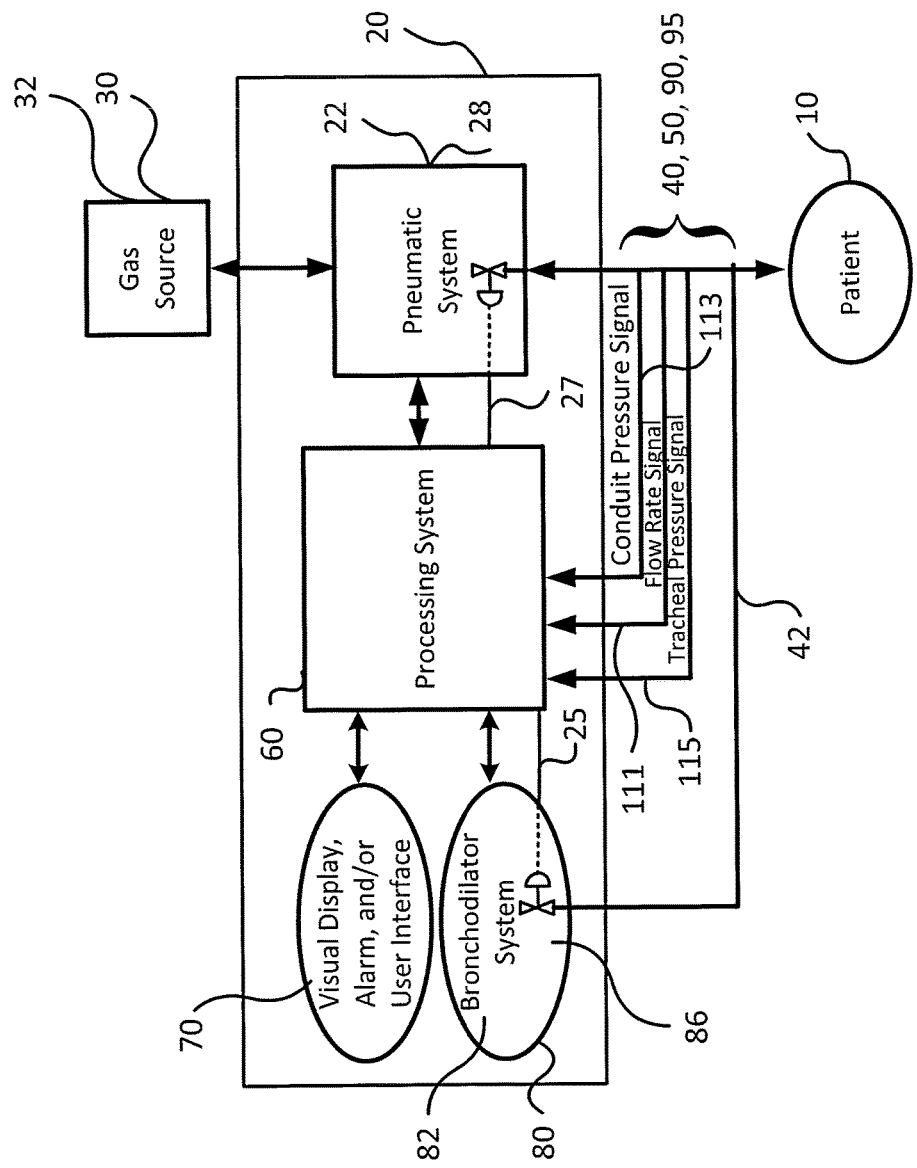
FIG. 3B is a block diagram of a medical ventilator according to another embodiment of the present invention.
Figure 4A:
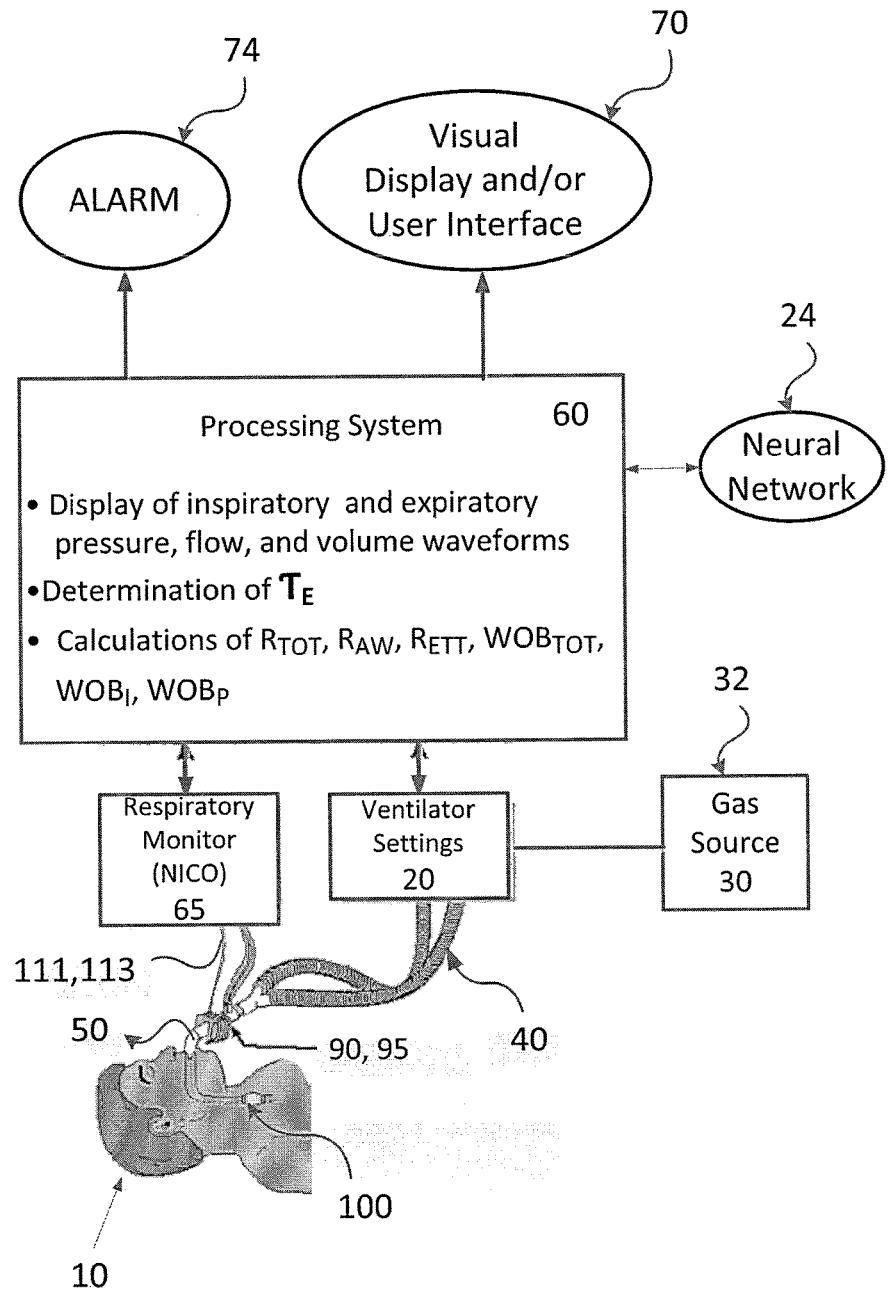
FIG. 4A is an illustration of a patient on an open loop system where resistance and work of breathing parameters are estimated in accordance with the subject invention.
Figure 4B:
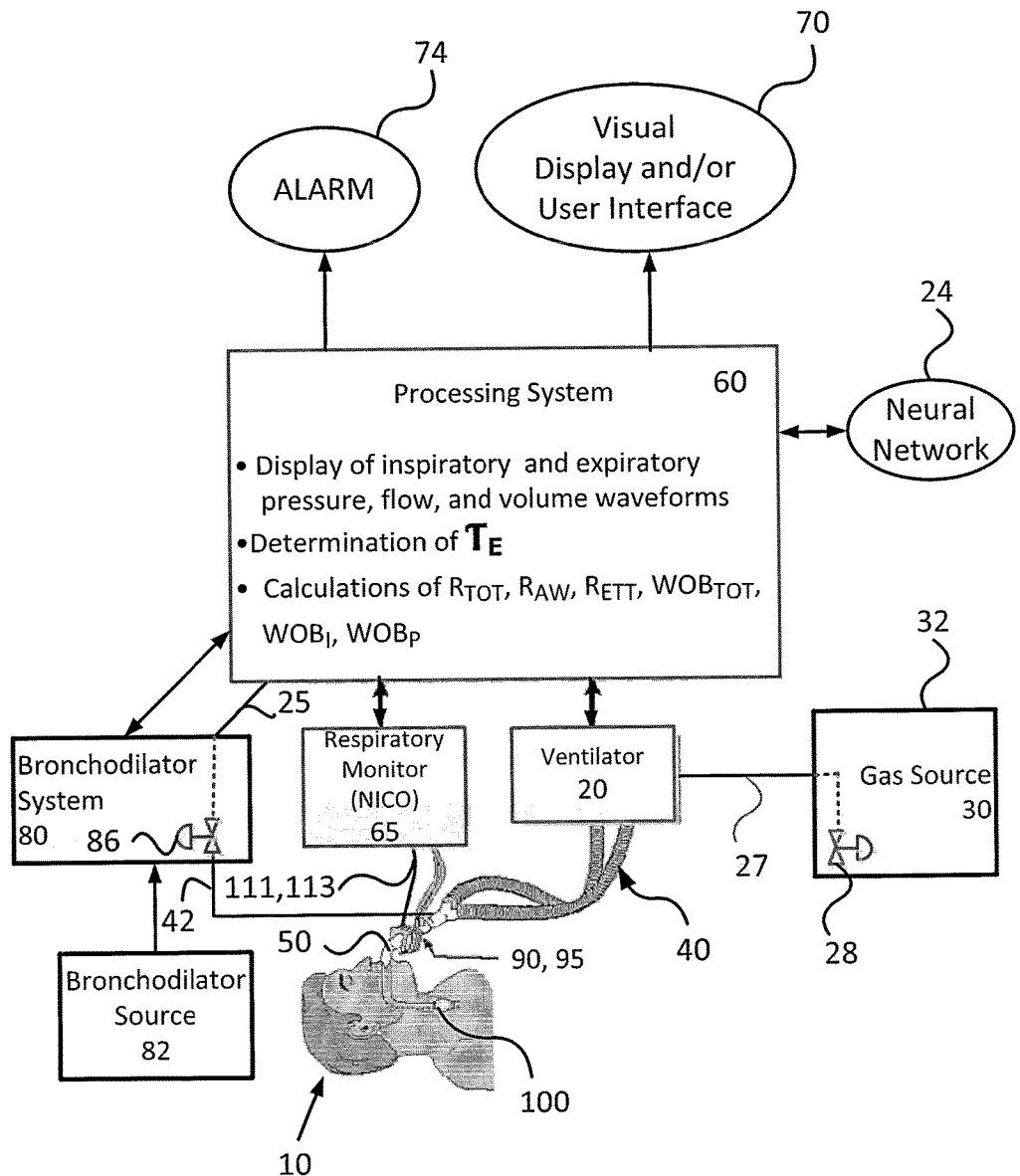
FIG. 4B is an illustration of a patient on a closed loop system where resistance and work of breathing parameters are estimated in accordance with the subject invention.

FIGS. 3 and 4 illustrate specific embodiments of the invention in accordance with the system illustrated in FIGS. 1 and 2. A patient is indicated at 10. A medical ventilator 20 is provided where the medical ventilator 20 is in flow/fluid communication with a gas source 30 of breathing gas 32 and a functionally open ventilator flow conduit 40 having a patient breathing attachment 50 in fluid communication with the lungs of the patient 10. The breathing gas 32 is pressure and/or flow rate controlled by a gas delivery means of the medical ventilator 20 so that the breathing gas 32 is delivered to the patient 10 at the selected ventilation level(s). The ventilator further comprises a conduit pressure sensing means disposed within the ventilator conduit 40 for sensing the pressure of the gas 32 within the ventilator conduit 40, a flow rate measuring means disposed within the ventilator conduit 40 for measuring the flow rate of the gas 32 within the ventilator conduit 40, a tracheal pressure sensing device, and a monitoring means operatively connected to the conduit pressure sensing means, the flow rate measuring means and the tracheal pressure sensing device for monitoring $R_{TOT}$, $R_{ETT}$, $R_{AW}$, $WOB_{TOT}$, $WOB_I$, and $WOB_P$ of the patient 10. FIGS. 3A and 4A are directed to an embodiment of the invention in which an open loop ventilator system is provided to the patient. FIGS. 3B and 4B are directed to closed-loop ventilator systems of the invention.

FIGS. 3A and 3B illustrate a ventilator 20 that includes a gas delivery means, preferably a pneumatic system 22, in fluid/flow communication with a gas source 30 of one or more breathing gases 32 and a ventilator conduit 40 and in operative connection with a monitoring means, preferably a processing system 60. The pneumatic system 22 can be of any design known in the art, including that disclosed in U.S. Pat. Nos. 4,838,259; 5,303,698; 5,400,777; 5,429,123; and 5,692,497, which are incorporated by reference herein.

The ventilator conduit 40 is in fluid/flow communication with the lungs of the patient 10 and can include a breathing attachment 50. The processing system 60 may be connected to a visual display, alarm and/or user interface 70 for visual and/or audio display of selected data and for user defined control of the ventilator 20 and/or bronchodilator system 80 and 86 (actuator/pump/nebulizer). The processing system 60 is also shown connected to a flow rate sensor 90, that measures the flow rate of the gas 32 within the ventilator conduit 40 and proximate the flow rate sensor 90, a conduit pressure sensor 95, that measures the pressure of the gas 32 proximate the pressure sensor 95, to a tracheal pressure sensing device 100, and to the pneumatic system 22 of the ventilator 20. The processing system 60 preferably performs operator-specific physiologic calculations on-line and in real-time, such as the calculation of the $R_{TOT}$, $R_{ETT}$, $R_{AW}$, $WOB_{TOT}$, $WOB_I$ and $WOB_P$ of the patient 10. In certain embodiments, the processing system 60 can also automatically regulate bronchodilator therapy and/or pressure support ventilation levels to support the physiologic needs of the patient 10.

As depicted in FIGS. 4A and 4B, a patient 10 requiring respiratory support is connected to a ventilator 20 and a respiratory monitor 65. An endotracheal tube is used as the patient breathing attachment 50. Preferably, at a distal end of the breathing attachment is an endotracheal pressure sensing device 100. Exhalation and inhalation conduits are connected to the proximal end of the patient breathing attachment 50 using a fitting called a Y (or wye)-piece. Thus, the patient breathing attachment and the inhalation and exhalation conduits form the ventilation conduit 40 that serves as inhalation and exhalation pathways for inhalation and exhalation gases entering and leaving, respectively, the patient's body.

Various continuous sensing and/or measuring means are coupled to the monitor 65 or to a processing system 60 of a ventilator 20 to facilitate continuous monitoring of $R_{TOT}$, $R_{ETT}$, $R_{AW}$, $WOB_{TOT}$, $WOB_I$ and $WOB_P$ of the patient 10. According to certain embodiments of invention, airway flow and pressure sensors 90, 95 along with possibly a carbon dioxide detector are disposed in the flow path of the gas within the ventilator conduit 40 at the Y-piece of the standard ventilator circuit. Each of these sensors 90, 95 are commercially available. These sensors measure the flow, pressure, and partial pressure of carbon dioxide in the gases that pass to and from the patient 10. In addition, a tracheal pressure sensing device 100, such as that disclosed in U.S. Pat. No. 5,752,921, which is incorporated herein by reference in its entirety, is provided. The raw signals from these sensors 90, 95, 100 are transmitted to a respiratory monitor 65 or processing system 60 of a ventilator 20 for preprocessing using analog and digital signal processing to clean the signal, remove sensor biases and offsets, etc.

The sensors 90, 95 are coupled to a processing system 60 to facilitate continuous monitoring of $R_{TOT}$, $R_{ETT}$, $R_{AW}$, $WOB_{TOT}$, $WOB_I$ and/or $WOB_P$ of a patient, particularly one in need of/receipt of bronchodilator therapy. The raw signals from these sensors 90, 95 are transmitted to a processing system 60 for preprocessing using analog and digital signal processing to clean the signal, remove sensor biases and offsets, etc.

In a particular embodiment, the airway flow sensor 90 generates a flow signal representative of the flow rate of the gas 32 proximate the flow rate measuring means. The flow signal generated from the flow rate measuring means is transmitted through a first analog-to-digital converter (A/D converter) to the processing system 60 or to the respiratory monitor 65 on flow signal line 111. The airway flow sensor 90 is preferably a differential pressure transducer and pneumotachometer. For example, the pneumotachometer may be comprised of a disposable, variable orifice provided by Acutach, Glen Medical Products or a fixed orifice type by Novametric Medical Systems. However, any flow rate sensor that is capable of sensing the flow rate within the ventilator conduit 40 and providing a signal representative of that flow rate may be substituted for the flow rate sensor 90. A rotameter, a respirometer, or a thermistor flow sensor, such as the Calculair Portable Electronic Spirometer by Hospal Medical Corporation, could be suitable substitutes.

The pressure sensor 95 generates a pressure signal representative of the pressure of the gas 32 proximate the pressure sensing means. The pressure sensor 95 is preferably a piezoresistive pressure sensor or a solid state pressure transducer. Still more preferred, if the airway flow sensor 90 is connected to a preferred differential pressure transducer, the differential pressure transducer may also concurrently sense the pressure of the gas at 90 thereby acting as the pressure sensor 95, and generate the requisite pressure signal. This is preferred as it requires only one sensor, the differential pressure transducer, to act as both the airway flow sensor and the pressure sensor 90, 95 and it allows the flow rate and pressure data gathering to be accomplished at a single site in the ventilator conduit 40.

The pressure signal from the pressure sensor 95 is transmitted through a second A/D converter to the microprocessor 60 or the respiratory monitor 65 on pressure signal line 113. This pressure signal may be transmitted through a digital or analog anti-aliasing filter [not shown] to remove noise above the Nyquist frequency before processing by the first A/D converter. The pressure sensor 95 may, for example, be comprised of commercially available pressure sensors from Honeywell or Sensym. However, it must be noted that any pressure sensor 95 capable of sensing the pressure of the gas 32 proximate the pressure sensor 95 and providing a signal representative of that pressure sensed could be substituted as the pressure sensor 95. For example, an aneroid pressure manometer could be a suitable substitute.

The tracheal pressure sensing device 100 preferably comprises sensors to measure pressure within the tracheal pressure sensing apparatus. The pressure signal from the tracheal pressure sensing device 100 is transmitted through another A/D converter to the microprocessor 60 or the respiratory monitor 64 on a pressure signal line 115. Data from the pressure sensors enable calculated (continuous) measurement of tracheal airway pressure. For example, tracheal airway pressure can be calculated from changes in pressure measured by the sensors of the tracheal pressure sensing apparatus when it surrounds the distal end of an endotracheal tube. Examples of such calculations are disclosed in U.S. Pat. No. 5,752,921 and are also incorporated herein by reference.

While a first and a second A/D converter are described for use with the flow rate sensor 90 and the pressure sensor 95, respectively, it is preferred that a single, multiplexed A/D converter [not shown] be used for converting the respective flow signal and pressure signal to digital format.

The preprocessed airway flow and pressure signals are then further processed by the processing system 60 to calculate a variety of other parameters from the flow and pressure (and $CO_2$, if available) data. For example, tidal volume is computed by integrating the flow into the patient over an inspiratory cycle; PIP is calculated by determining the maximum pressure during a breath; $P_{0.1}$ is calculated by measuring the change in airway pressure during the first tenth of a second of a breath; work of breathing parameters can be calculated by adaptively fitting a model, such as a linear model, to the airway pressure, flow, and volume signals; etc.

Preferably, the respiratory monitor 65 or the processing system 60 comprises a microprocessor. The microprocessor may be analog or digital and should contain circuits to be programmed for performing mathematical functions such as waveform averaging, amplification, linearization, signal rejection, differentiation, integration, addition, subtraction, division and multiplication, where desired. Circuits or programs for performing these functions are conventional and well known, and they form no part of the present invention. A microprocessor is preferred over dedicated analog or digital processors because it has the flexibility to be programmed to store and analyze data and to provide hard copy in many forms. If an analog microprocessor is used, the first and second A/D converters or the single, multiplexed A/D converter are not required, because the analog microprocessor requires the flow signal and the pressure signal to be in the nonconverted analog format.

The parameters and data derived from the signals produced by the flow rate sensor 90, the pressure sensor 95, and the tracheal pressure sensing device 100 can be stored in the memory of the microprocessor at user-defined rates for as-needed retrieval and analysis. The airway flow rate, pressure, and tracheal pressure sensors 90, 95, 100 may continually monitor/sense the flow rate and the pressure of the breathing gas 32 proximate the respective sensors. The parameters and data may include: peak inflation pressures at the ventilator Y-piece and tracheal end of the endotracheal tube, flow rate, peak inspiratory flow rate, respiratory muscle pressure (Pmus(t)), average respiratory muscle pressure during the inspiratory period, average respiratory muscle pressure over a serial number of breaths, inspiratory plateau pressure (Pplt) or static elastic recoil pressure, inspiratory tidal volume, baseline airway pressure, PEEP, mean airway pressure, spontaneous and ventilation breathing frequency, and spontaneous, ventilator, and total minute ventilation.

The memory may be, for example, a floppy disk drive or internal RAM or hard drive of the associated microprocessor. These data may be stored to provide a permanent log of all events related to the patient's course on the ventilator 20, and allow for on-line and retrospective analysis of pulmonary function, i.e., compliance of the respiratory system (Crs), $R_{TOT}$, and gas 32 analysis as a function of time. Furthermore, the microprocessor can perform operator-specific physiologic calculations on-line and in real-time, such as the calculation of the $R_{TOT}$, $R_{ETT}$, $R_{AW}$, $WOB_{TOT}$, $WOB_I$ and $WOB_P$ of the patient 10. Alternatively, the data can be stored for later analysis and review.

Further embodiments of the subject invention are directed to a closed loop system, such as those illustrated in FIGS. 3B and 4B. The closed-loop system is similar to the open-loop system (such as those of FIGS. 3A and 4A) with the exception that the processing system 60 of the closed-loop system is also connected to a bronchodilator delivery system 80 and has the ability to direct delivery of bronchodilator therapy and/or ventilation to the patient. In the closed loop system, the processing system 60 automatically determines, sets, and delivers the bronchodilator therapy that will maintain the patient's $R_{AW}$ within a desired predetermined $R_{AW}$ range. In addition, the processing system 60 of the closed loop system may automatically determine, set and deliver necessary ventilator support to maintain a desired work of breathing range (e.g. manipulating the pressure support ventilation level of the pneumatic system).

As illustrated in FIGS. 3B and 4B, the bronchodilator delivery system 80 is in fluid communication with the ventilator conduit via a bronchodilator supplier 42. The bronchodilator delivery system 80 controls a bronchodilator source 82 so that a bronchodilator is delivered to the patient 10 when such treatment is required. The administration of the bronchodilator from the bronchodilator source 82 is controlled by a bronchodilator delivery means of the bronchodilator system 80. The processing system 60 is operatively coupled to a bronchodilator delivery system 80 via a regulating means for regulating the bronchodilator(s) to be administered to the patient 10.

As one skilled in the art would appreciate, the bronchodilator system 80 and the operative connection of that bronchodilator system 80 to the source of bronchodilator(s) 82 may be any design known in the art that has at least one actuator that is capable of being operatively coupled, preferably electrically coupled, to the processing system 60 for controlling the bronchodilator(s) to be administered to the patient 10.

The regulating means of the bronchodilator system 80 preferably comprises at least one driver circuit 25 electrically coupled to the processing system 60 that determines and monitors $R_{AW}$ and to at least one actuator 86 of the bronchodilator source 82. The actuator 86 of the bronchodilator source 82 controls the bronchodilator(s) to be administered to the patient 10 via bronchodilator supplier 42. The driver circuit 25 adjusts the actuator 86, as required, based on electrical signals received from the processing system 60, thus regulating the bronchodilator to be supplied to the patient 10. The driver circuit may be a signal line. In certain embodiments, the actuator 86 is in the form of a binary valve, which is in either a fully open or fully closed position.

In certain embodiments, processing system 60 is coupled to the pneumatic system via driver circuit(s) 27 and to at least one actuator 28. The actuator(s) 28 controls the delivery of appropriate ventilation to the patient 10. The driver circuit(s) 27 adjusts the actuator(s) 28, as required, based on electrical signals received from the processing system 60, thus regulating the pressure and/or flow rate of breathing gas 32 supplied to the patient 10. For example, the ventilator 20 may include two actuators, an inhalation conduit actuator and an exhalation conduit actuator, that is coupled to the processing system via driver circuits. Each actuator preferably controls and adjusts the pressure and/or flow of breathing gas 32 exiting the ventilator 20. The processing system 60 can control each actuator to ensure the pressure and/or flow of gas is delivered to the patient 10 at a desired pressure support ventilation level to the patient via the ventilator conduit 40. The actuator(s) 28 can be a binary valve, which is in either a fully open or fully closed position. Alternatively, the actuator(s) 28 can be a proportional valve, in which the passage of the actuator(s) 28 is opened proportionally corresponding to various desired flow rates. The proportional valve is preferably a high speed, flow regulating solenoid valve for regulating the flow of gas 32 from the gas source 30.

The circuitry for monitoring and/or treating the patient 10 can be embodied by other circuitry well know in the art. In addition, while the respiratory monitor 65 and the processing system 60 have been described as having a single microprocessor for monitoring and processing signals representing pressure and flow rate of the gas 32 proximate the respective sensors 90, 95, 100, and for controlling the ventilator 20 and/or bronchodilator system 80 (where applicable), it should be understood that two or more microprocessors could be used dedicated to the individual functions. In addition, the functions of the microprocessor could be achieved by other circuits, such as an application specific integrated circuit (ASIC), digital logic circuits, a microcontroller, or a digital signal processor.

Further, the processing system 60 (and ventilator 20, if the processing system is a part of the ventilator 20) may have a visual display, alarm and/or user interface 70. In the preferred embodiment, a user interface is provided that is a membrane keypad, a keyboard, and/or other suitable input device. An operator of the ventilator may provide the processing system 60, via the user interface 70, with any number of desirable input parameters, such as patient identification information, patient age, patient weight, patient health, or any other desired patient statistics.

In one embodiment, the operating clinician may input one or more of the desired predetermined $R_{AW}$, $R_{ETT}$, $WOB_{TOT}$, $WOB_P$ and/or $WOB_I$ ranges so that the microprocessor may compare the $R_{AW}$, $R_{ETT}$ $WOB_{TOT}$, $WOB_P$ and/or $WOB_I$ derived from the airway flow, pressure and tracheal pressure sensors 90, 95, 100 as described herein against the input predetermined $R_{AW}$, $R_{ETT}$ $WOB_{TOT}$, $WOB_P$ and/or $WOB_I$ ranges or values. Predetermined reference data, such as the inspiratory and expiratory pressure, flow and volume of the respiratory system, may also be input into the processing system 60. Alternatively, such reference data may be calculated by the processing system 60 (e.g., based on population averages).

According to the subject invention, the components for closed loop delivery of bronchodilator(s) can be physically independent from the closed loop delivery of ventilation to the patient. Alternatively, these components can be presented in various combinations to form a single component. For example, a ventilator may contain all of the components for closed loop delivery of bronchodilator(s) and ventilation or a ventilator may include the components for the closed loop delivery of bronchodilator(s) without the closed loop delivery of ventilation, or vice versa.

The processing system 60 (and ventilator 20, if the processing system is a part of the ventilator 20) may further have a visual display 70 for outputting and displaying electronic output signals generated from the microprocessor(s). The preferred electronic output signals may include at least one of: the signal 90, 95, 100 data, the determined $\tau_E$, the determined $R_{TOT}$, $R_{ETT}$, $R_{AW}$, $WOB_{TOT}$, $WOB_I$ and $WOB_P$ of the patient 10, and the target $R_{AW}$, $R_{ETT}$ $WOB_{TOT}$, $WOB_I$ and/or $WOB_P$ ranges or values for concurrent review by the operator of the ventilator 20. The visual display 70 may vary the pattern of the display in accordance with the contents of the electronic output signals from the microprocessor. Preferably, the visual display 70 is a monitor but any means for displaying electronic output signals known to one skilled in the art may be used.

Still further, the processing system 60 (and ventilator 20, if the processing system is a part of the ventilator 20) may have an alarm means for alerting the operator of either a failure in the ventilator 20, such as a power failure, or if bronchotherapy and/or a different pressure support ventilation level needs to be administered to the patient or the endotracheal tube needs to be assessed. Preferably, the alarm means comprises a visual and/or audio alarm but any means for alerting the operating clinician known to one skilled in the art may be used. Of course, it is desired to use a backup power supply, such as a battery.

In an aspect of the invention, a neural network 24 may be provided to model the parameters so that a ventilator 20 (or bronchodilator system 80) may be controlled through a controller. The neural network 24 may be included within the processing system 60.

Figure 5:
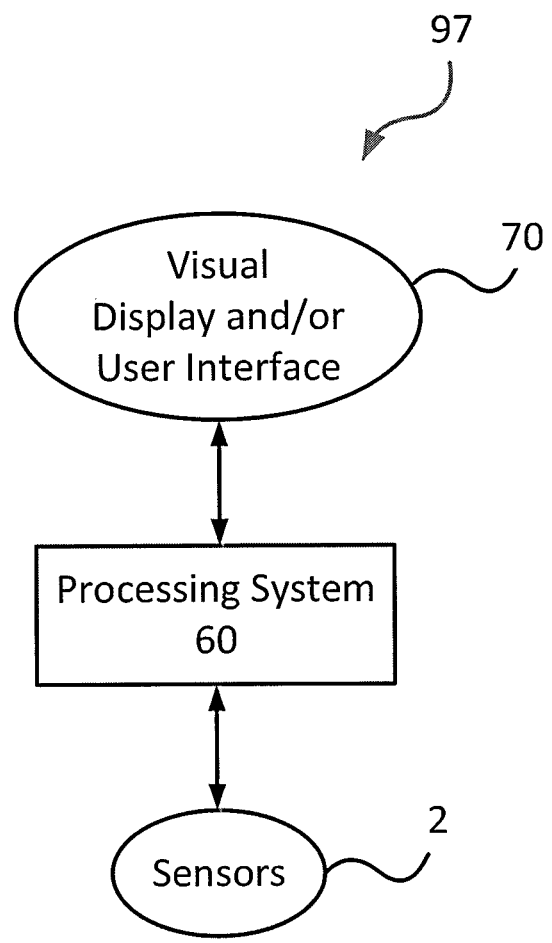
FIG. 5 is an illustration of a stand alone bronchodilation monitoring device.

FIG. 5 illustrates a bronchodilator therapy system 97. The system 97 includes visual display and/or user interface 70, a processing system 60, and at least one sensor 2, such as an airflow measuring device inserted in the breathing circuit to monitor the pressure, flow, volume, and end tidal CO2 values from the patient. The display and/or user interface 70 provides a health care clinician with patient respiratory parameters such as the compliance, resistance, and work of breathing. The processing system 60 may be configured to provide indications of when bronchodilator therapy or the endotracheal tube cleaning may need to be addressed. The system 97 can be provided as a single, self-contained device. Alternatively, the system may be built into a ventilator or built into a respiratory monitor. In other embodiments, the sensor(s) 2 may be those used by a ventilator and/or respiratory monitor, wherein output signals from the sensor(s) are communicated to and analyzed by a processing system 60 that is separate from the ventilator or respiratory monitor.

Figure 6:
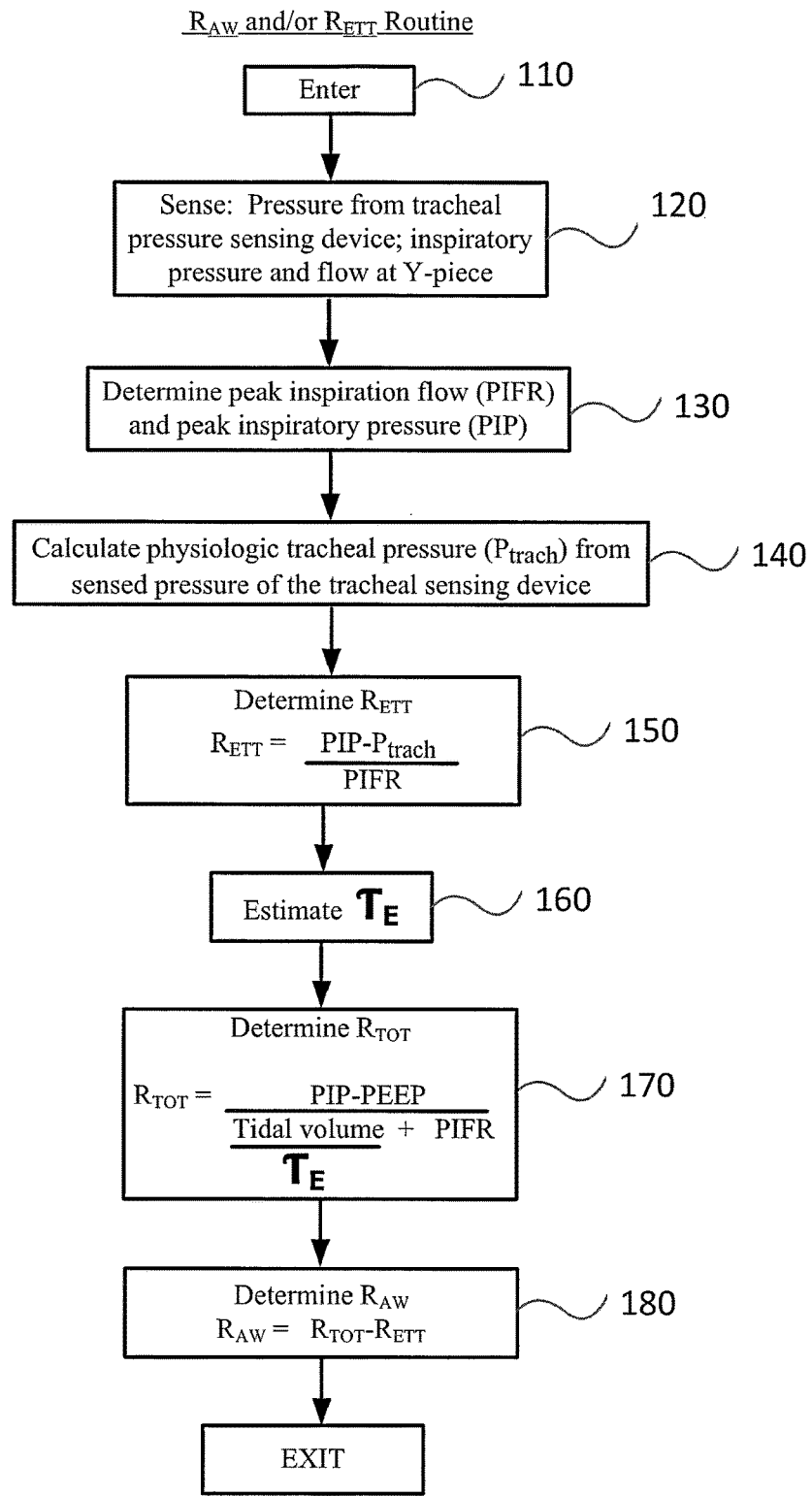
FIG. 6 is a flow chart illustrating the preferred sequence for carrying out the determination of the $R_{AW}$ and/or $R_{ETT}$ of the patient.

FIG. 6 illustrates how $R_{AW}$ and $R_{ETT}$ are determined. When the $R_{AW}$ and $R_{ETT}$ measurement process is started, as shown in 110, signals from the sensors 90, 95, 100 are provided to the processing system 60 to measure tracheal pressure and inspiratory pressure and flow at the Y-piece as shown in step 120. Referring to step 130, the peak inspiratory flow and peak inspiratory pressure is determined. In step 140, a calculation of physiologic tracheal pressure is determined. Thence, in steps 150, 160, 170 and 180, the $R_{TOT}$, $R_{ETT}$ and $R_{AW}$ of the patient can be determined by applying the equations described above.

Figure 7A:
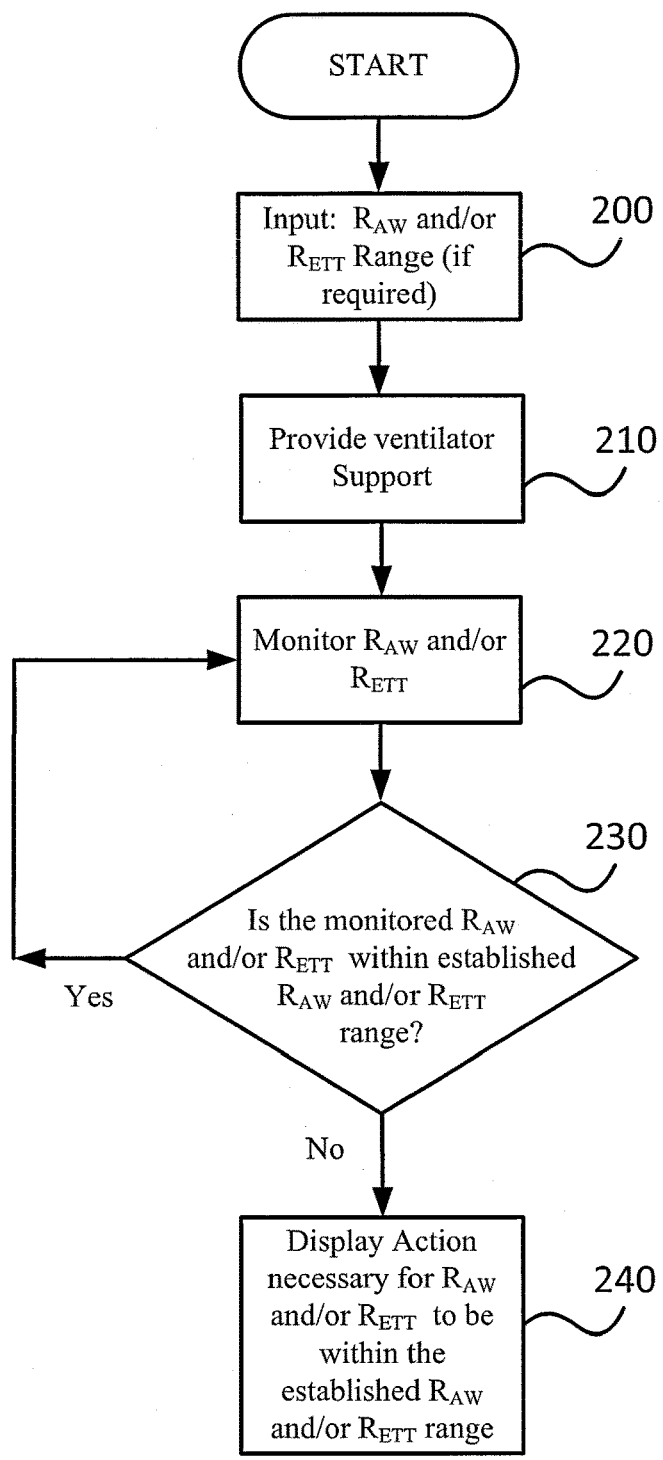
FIG. 7A is a flow chart illustrating a general sequence of steps for carrying out an open-loop operation for assessing resistance in accordance with the present invention.

Referring now to FIG. 7A, in the open-loop operation of an embodiment of the present invention, the processing system 60 is responsive to the airway flow, pressure and tracheal pressure signals to continually determine the $R_{AW}$ and/or $R_{ETT}$ of the patient 10. The processing system compares the determined $R_{AW}$ and/or $R_{ETT}$ of the patient 10 to a predetermined $R_{AW}$ and/or $R_{ETT}$ range and generates a response signal based on the comparison. The processing system generates the response signal when the patient's $R_{AW}$ and/or $R_{ETT}$ are/is not within the predetermined $R_{AW}$ and/or $R_{ETT}$ range. Then, in response to the response signal of the processing system, the alarm means may generate an alarm that is suitable for alerting an operator that the patient's $R_{AW}$ and/or $R_{ETT}$ is not within the predetermined $R_{AW}$ and/or $R_{ETT}$ range.

The processing system, when it has determined $R_{AW}$ and/or $R_{ETT}$ is outside the predetermined $R_{AW}$ and/or $R_{ETT}$ range, can generate a signal in response thereto and/or store the determined $R_{AW}$ and/or $R_{ETT}$. This target $R_{AW}$ and/or $R_{ETT}$ range is displayed to the operator to advise them of the appropriate $R_{AW}$ and/or $R_{ETT}$. In the open-loop operation, in response to the level signal of the processing system that the $R_{AW}$ and/or $R_{ETT}$ is not within the predetermined range, a proposed action necessary for addressing the change to $R_{AW}$ and/or $R_{ETT}$ is displayed to the operator. For example, where $R_{AW}$ increases outside the predetermined $R_{AW}$ range, proposed bronchotherapy for the patient is displayed to the operator. As another example, where $R_{ETT}$ increases outside the predetermined $R_{ETT}$ range, proposed assessment of the endotracheal tube for patency is displayed to the operator Thus, in the open-loop operation of the present invention, upon the input of the desired predetermined $R_{AW}$ and/or $R_{ETT}$ range in Block 200, the ventilator 20 begins to provide ventilation, as shown in Block 210. The monitoring means, in Block 220, then monitors the $R_{AW}$ and/or $R_{ETT}$ of the patient 10 and, when the $R_{AW}$ and/or $R_{ETT}$ is not within the desired $R_{AW}$ and/or $R_{ETT}$ range, determined, in Block 230, a display regarding the proposed action that would maintain the patient's $R_{AW}$ and/or $R_{ETT}$ within the desired predetermined $R_{AW}$ and/or $R_{ETT}$ range is provided in Block 240. Concurrent with the display that the $R_{AW}$ and/or $R_{ETT}$ is not within the predetermined $R_{AW}$ and/or $R_{ETT}$ range, the operator may be alerted via the alarm means that the measured $R_{AW}$ and/or $R_{ETT}$ is not within the predetermined $R_{AW}$ and/or $R_{ETT}$ range. Subsequent to advising the operator of appropriate action to take, in Block 240, or determination that the $R_{AW}$ and/or $R_{ETT}$ is within the predetermined range, in Block 230, the processing system then steps back to Block 220 to continuously monitor $R_{AW}$ and/or $R_{ETT}$.

In certain embodiments, the open loop operation is performed using a decision support module 6, such as that illustrated in FIG. 2. For example, a $R_{AW}$ and/or $R_{ETT}$ manager is coupled to the decision support module 6, wherein the $R_{AW}$ and/or $R_{ETT}$ manager is configured to determine estimated $R_{AW}$ and $R_{ETT}$ values from sensor outputs. $R_{AW}$ and/or $R_{ETT}$ manager output is then provided to the decision support module 6 that is configured to monitor or trend estimated $R_{AW}$ and/or $R_{ETT}$ values during different situations, such as monitoring (and automatically optimizing) the endotracheal tube for suctioning/replacement (see FIG. 7B); monitoring start, stop, increase, decrease or change in bronchodilator therapy and automatically optimizing bronchodilator therapy (see FIG. 7C); monitoring the compliance and resistance of the patient and display potential issues; etc. In addition to a $R_{AW}$ and/or $R_{ETT}$ manager, other managers may be implemented. For example, a cuff pressure manager may be coupled to the decision support module, wherein the decision support module could also monitor whether the cuff pressure is too high or too low (e.g., which is associated with leaks) and automatically provide appropriate action to address changes to the cuff pressure (see FIG. 7D).

Figure 7B:
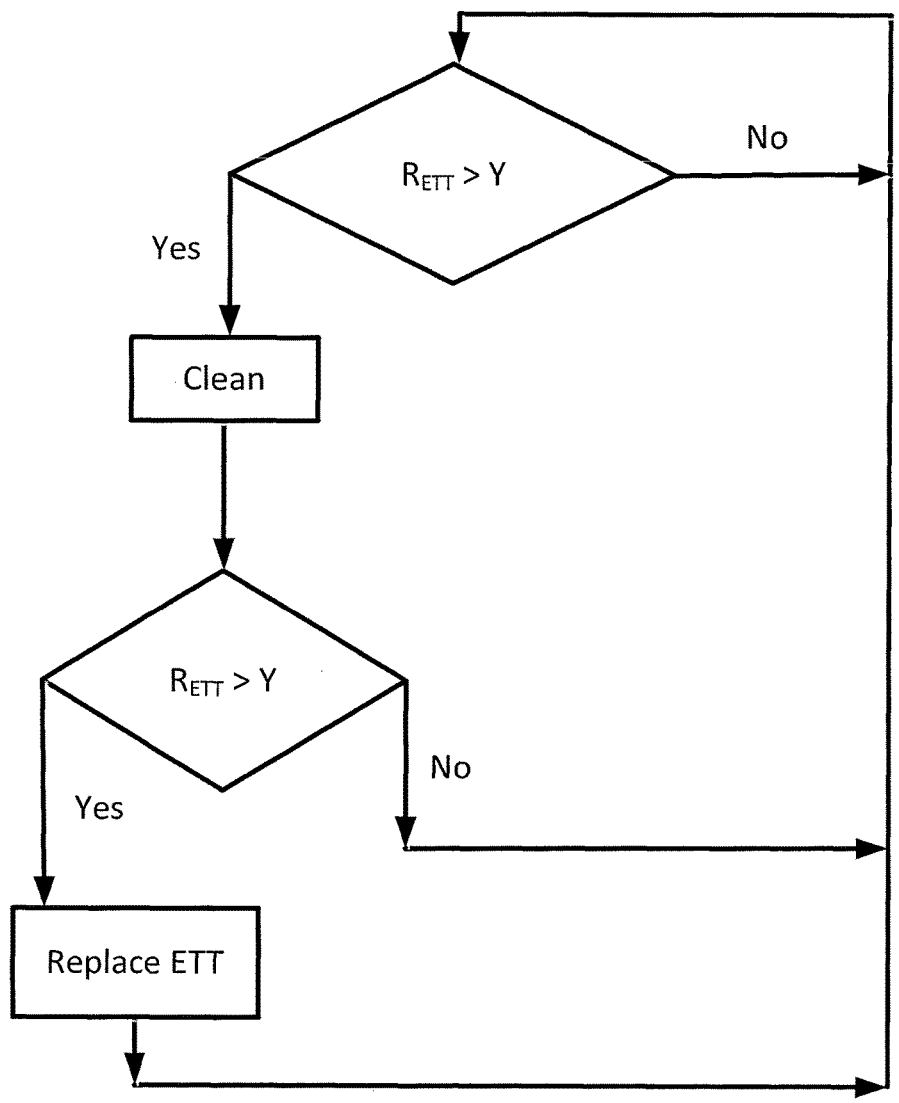
FIGS. 7B-7D are flow charts illustrating general sequence steps that can be performed by a decision support module.

FIG. 7B shows a flowchart of the steps performed by a decision support module that is configured to monitor endotracheal tube resistance. Y is the endotracheal tube resistance threshold between low endotracheal tube resistance and high endotracheal tube resistance. When the endotracheal tube resistance is greater than the endotracheal tube resistance threshold, the decision support module provides notice to the user that the endotracheal tube is to be cleaned and/or replaced, if cleaning the endotracheal tube has not decreased the endotracheal tube resistance. The value of Y will vary with the size of the endotracheal tube. Smaller tubes inherently have higher resistances, even when clean. An example would be that Y is 8 cm H20/L/S for an 8.0 ET-tube (adult) and a 5.0 ET-tube (child) might be 15 cm H20/L/s or higher.

Figure 7C:
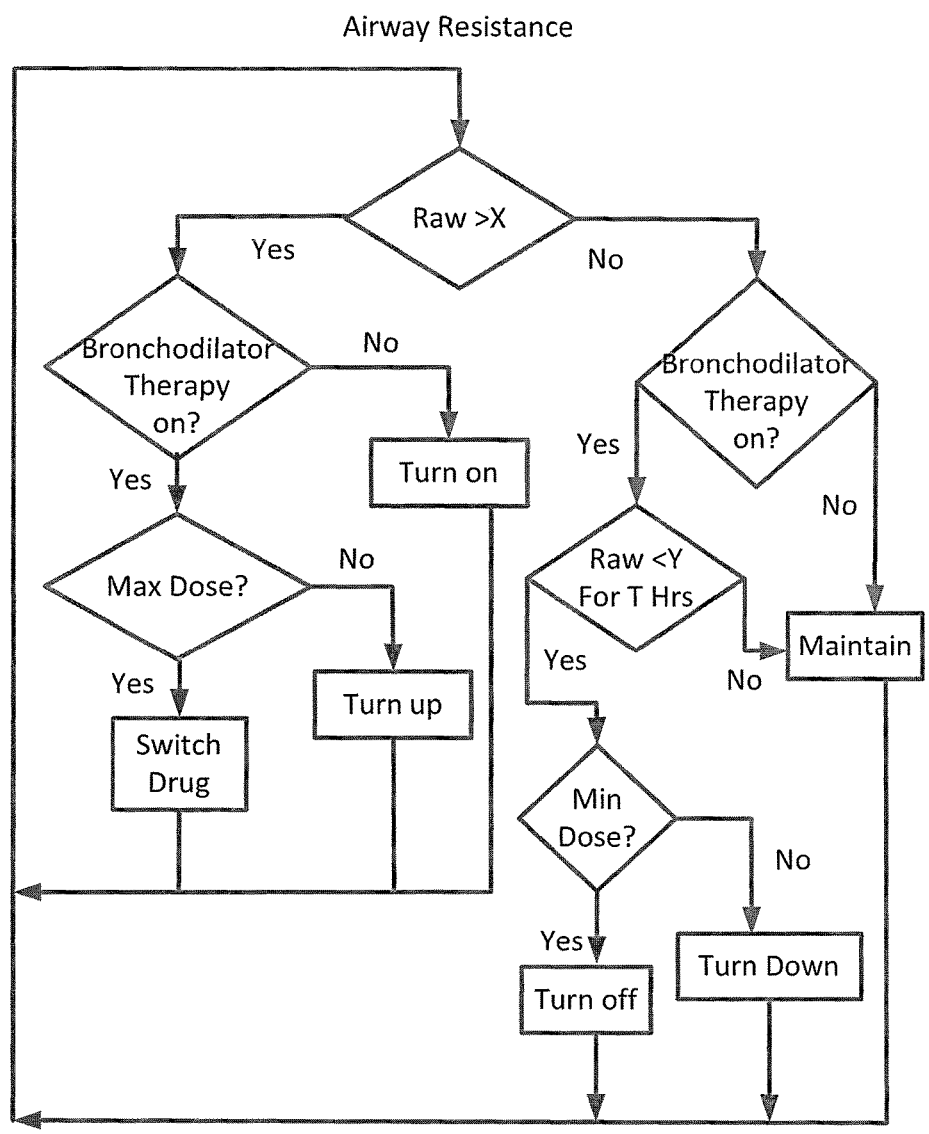

FIG. 7C shows a flowchart of the steps performed by a decision support module that is configured to monitor airway resistance and to provide clinical suggestions for bronchodilator therapy when needed. Max Dose is the maximum therapeutic dose the clinician would administer to the patient for the given bronchodilator. Min Dose is the minimum therapeutic dose the clinician would administer to the patient for the given bronchodilator. X is the airway resistance threshold between low airway resistance and high airway resistance (X would likely be between 5 and 10 cm H20/L/S). Y is the acceptable airway resistance threshold, in some cases most will set X=Y. T is the minimum dose time where the patient will remain at the minimum dose for T hours before decreasing the dose. In this embodiment, if airway resistance is high, then the decision support module provides notice to the user that bronchodilator therapy is needed. If bronchodilator therapy is already being provided, the decision support module can provide a suggestion to the user that the bronchodilator therapy is to be increased unless it is already set at maximum. If already at maximum, the decision support module can provide a suggestion to the user to consider other drugs for use in the bronchodilator therapy. Where airway resistance is low, the decision support module can provide a suggestion to the user to consider decreasing bronchodilator therapy, particularly if the resistance has been low for an extended period of time.

Figure 7D:
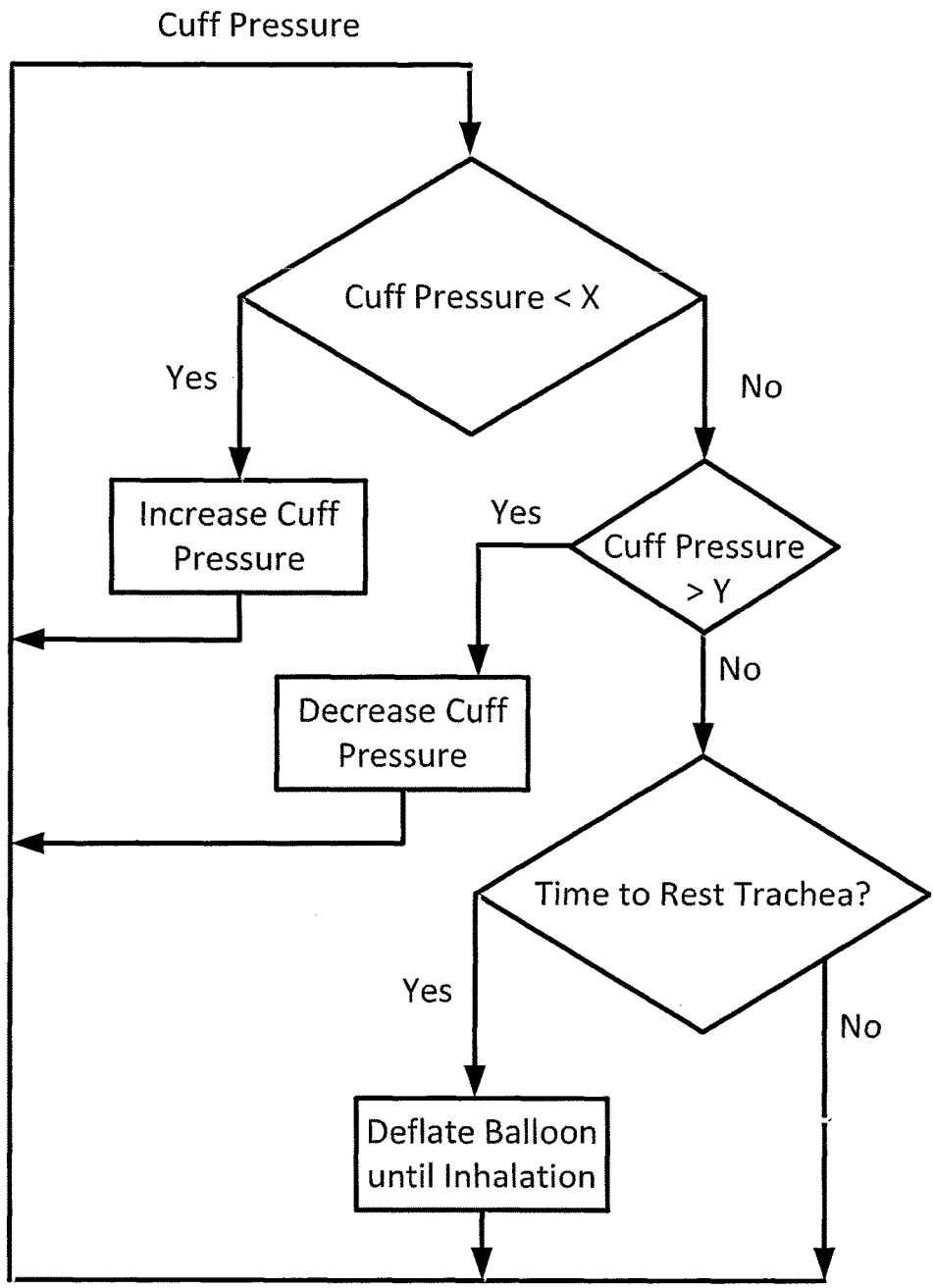

FIG. 7D shows a flowchart of the steps performed by a decision support module that is configured to monitor cuff pressure and to provide clinical suggestions to address changes to the cuff pressure. X is the minimum acceptable cuff pressure (typically 20 cm H20). Y is the maximum acceptable cuff pressure (typically 30 cm H20). Where the cuff pressure falls below X, the decision support module can provide a suggestion to the user to increase cuff pressure. Where the cuff pressure is greater than Y, the decision support module can provide a suggestion to the user to decrease cuff pressure. Maintaining proper cuff pressure (typically between 20 and 30 cm H20) has been shown to improve patient outcome. Cuff pressures that are lower than desired can lead to ventilator associated pneumonia and cuff pressures higher than desired can lead to tracheal damage.

Figure 8:
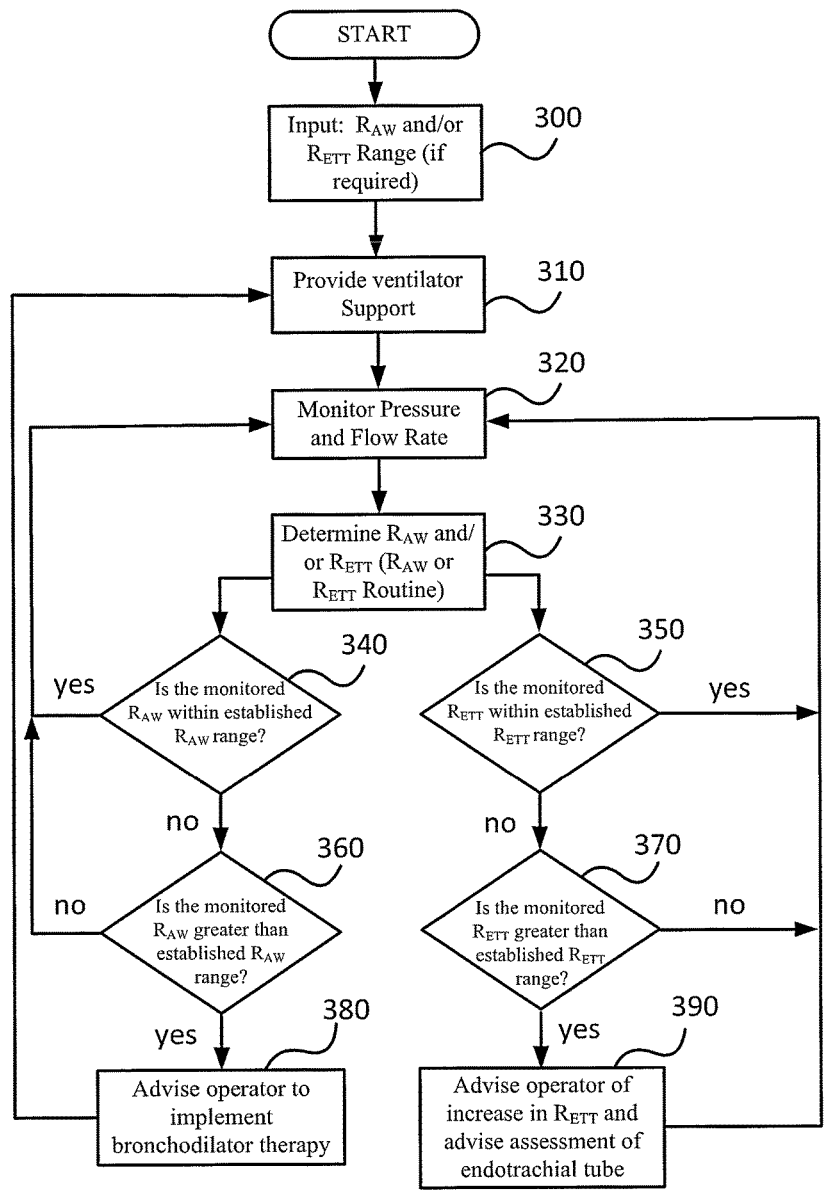
FIG. 8 is a flow chart illustrating a preferred sequence of steps for carrying out an open-loop operation for assessing resistance in accordance with the present invention.

FIG. 8 shows a flowchart for a preferred embodiment of the software that controls the open-loop operation. The program continues to execute as long as the ventilator 20 or processing system 60 is not reset. At step 300, the input parameters are selected, such as the desired predetermined $R_{AW}$ and/or $R_{ETT}$ range. At step 310, the ventilator 20 supplies breathing gas 32 to the patient 10 via the ventilator conduit 40. At step 320, the airway flow, pressure and tracheal pressure is measured. At step 330, the $R_{AW}$ and/or $R_{ETT}$ of the patient 10 is calculated from the sensed pressure, airway flow rate and tracheal pressure. In steps 340 and 350, it is determined if the measured $R_{AW}$ and/or $R_{ETT}$, respectively, are within the predetermined $R_{AW}$ and/or $R_{ETT}$ range. If the $R_{AW}$ and/or $R_{ETT}$ is within the predetermined range, the processing system then steps back to Block 320 to continuously monitor $R_{AW}$ and/or $R_{ETT}$. If the $R_{AW}$ and/or $R_{ETT}$ is not within the predetermined $R_{AW}$ and/or $R_{ETT}$, then it is determined in Blocks 360 and 370 whether $R_{AW}$ and/or $R_{ETT}$ is greater than the predetermined $R_{AW}$ and/or $R_{ETT}$. If the $R_{AW}$ and/or $R_{ETT}$ is not greater than the predetermined $R_{AW}$ and/or $R_{ETT}$ range, the processing system then steps back to Block 320 to continuously monitor $R_{AW}$ and/or $R_{ETT}$. If the $R_{AW}$ and/or $R_{ETT}$ is greater than the predetermined $R_{AW}$ and/or $R_{ETT}$ range, in Blocks 380 and 390 the proposed actions necessary to address increased $R_{AW}$ and/or $R_{ETT}$ and treat the patient are displayed.

The ventilator 20 or processing system 60 may also alarm the operator that the patient's $R_{AW}$ and/or $R_{ETT}$ are not within the desired $R_{AW}$ and/or $R_{ETT}$ range. After displaying the proposed actions 380,390, the processing system 60 steps back to step 320 to continuously monitor $R_{AW}$ and/or $R_{ETT}$.

Figure 9:
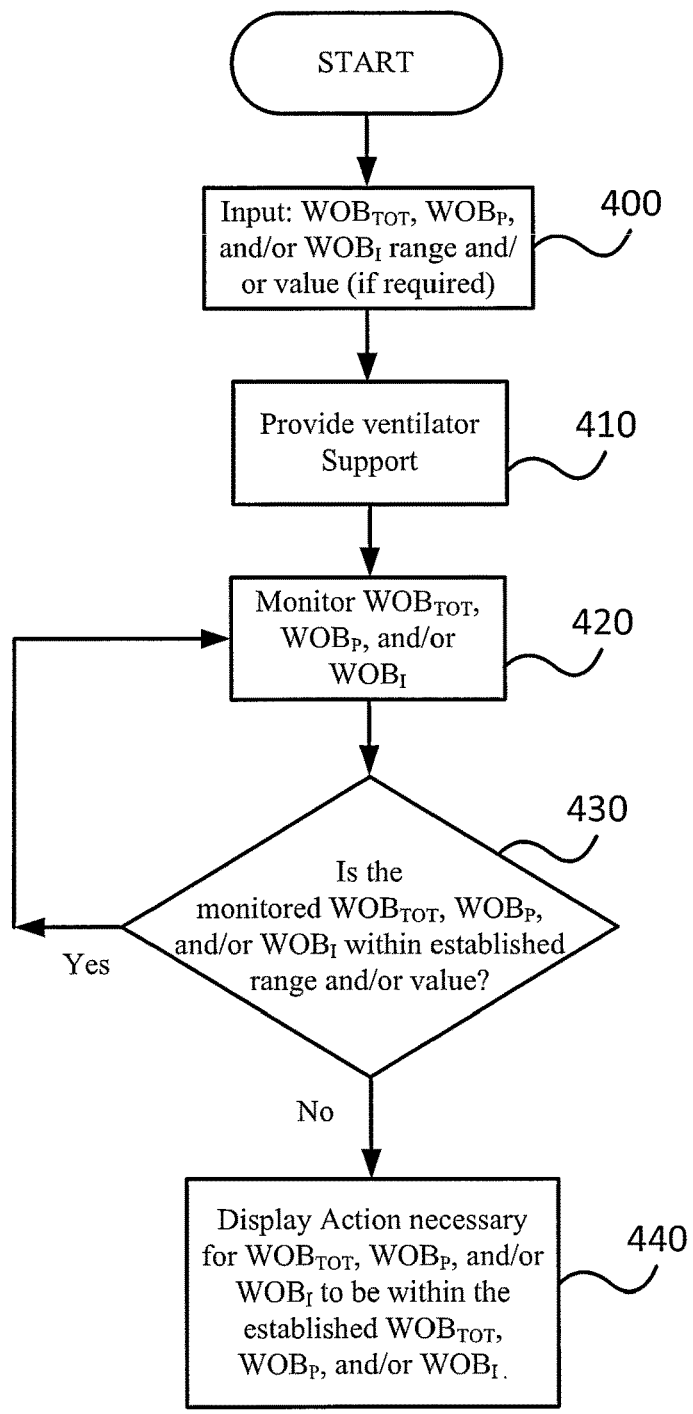
FIG. 9 is a flow chart illustrating a general sequence of steps for carrying out an open-loop operation for assessing work of breathing in accordance with the present invention.

Referring now to FIG. 9, the open-loop operation of an embodiment of the present invention includes the processing system 60 that is responsive to the airway flow, pressure and tracheal pressure signals to continually determine the $WOB_{TOT}$, $WOB_P$ and/or $WOB_I$ of the patient 10. As a first step, the processing system compares the determined $WOB_{TOT}$, $WOB_P$ and/or $WOB_I$ of the patient 10 to a predetermined $WOB_{TOT}$, $WOB_P$ and/or $WOB_I$ range or value and generates a response signal based on the comparison. In general, the desirable predetermined $WOB_{TOT}$ will be in a range of about 5-10 Joules/min. and the desirable predetermined $WOB_I$ value is zero. However, as one skilled in the art will appreciate, any desired $WOB_{TOT}$, $WOB_P$ and/or $WOB_I$ value or range may be inputted into the processing system 60.

The processing system generates the response signal when the patient's $WOB_{TOT}$, $WOB_P$ and/or $WOB_I$ are/is not within the predetermined $WOB_{TOT}$, $WOB_P$ and/or $WOB_I$ range/value. Then, in response to the response signal of the processing system, the alarm means may generate an alarm that is suitable for alerting an operator that the patient's $WOB_{TOT}$, $WOB_P$ and/or $WOB_I$ is not within the predetermined $WOB_{TOT}$, $WOB_P$ and/or $WOB_I$ range/value.

The processing system, when it has determined $WOB_{TOT}$, $WOB_P$ and/or $WOB_I$ is outside the predetermined $WOB_{TOT}$, $WOB_P$ and/or $WOB_I$ range/value, can generate a signal in response thereto and/or store the determined $WOB_{TOT}$, $WOB_P$ and/or $WOB_I$. This target $WOB_{TOT}$, $WOB_P$ and/or $WOB_I$ range/value is displayed to the operator to advise them of the appropriate $WOB_{TOT}$, $WOB_P$ and/or $WOB_I$. In the open-loop operation, in response to the level signal of the processing system that the $WOB_{TOT}$, $WOB_P$ and/or $WOB_I$ is not within the predetermined range or is not at the predetermined value, a proposed action necessary for addressing the change to $WOB_{TOT}$, $WOB_P$ and/or $WOB_I$ is displayed to the operator. For example, where $WOB_{TOT}$ and $WOB_P$ increase outside the predetermined $WOB_{TOT}$ and $WOB_P$ range, a proposed increase in the pressure support ventilation level for the patient is displayed to the operator. As another example, where $WOB_I$ increases outside the predetermined $WOB_I$ value of zero, proposed action for pressure support ventilation is displayed to the operator.

Thus, in the open-loop operation of the present invention, upon the input of the desired predetermined $WOB_{TOT}$, $WOB_P$ and/or $WOB_I$ range or value in Block 400, the ventilator 20 begins to provide ventilation, as shown in Block 410. Preferably, the predetermined $WOB_{TOT}$ range is 5-10 J/min. and the predetermined $WOB_I$ value is zero. The monitoring means, in Block 420, then monitors the $WOB_{TOT}$, $WOB_P$ and/or $WOB_I$ of the patient 10 and, when the $WOB_{TOT}$, $WOB_P$ and/or $WOB_I$ is not within the desired $WOB_{TOT}$, $WOB_P$ and/or $WOB_I$ range/value as determined in Block 430, a display regarding the proposed action that would maintain the patient's $WOB_{TOT}$, $WOB_P$ and/or $WOB_I$ within the desired predetermined $WOB_{TOT}$, $WOB_P$ and/or $WOB_I$ range is provided in Block 440. Concurrent with the display that the $WOB_{TOT}$, $WOB_P$ and/or $WOB_I$ is not within the predetermined $WOB_{TOT}$, $WOB_P$ and/or $WOB_I$ range/value, the operator may be alerted via the alarm means that the measured $WOB_{TOT}$, $WOB_P$ and/or $WOB_I$ is not within the predetermined $WOB_{TOT}$, $WOB_P$ and/or $WOB_I$ range/value. Subsequent to advising the operator of appropriate action to take, in Block 240, or determination that the $WOB_{TOT}$, $WOB_P$ and/or $WOB_I$ is within the predetermined range/value, in Block 430, the processing system then steps back to Block 420 to continuously monitor $WOB_{TOT}$, $WOB_P$ and/or $WOB_I$.

Figure 10:
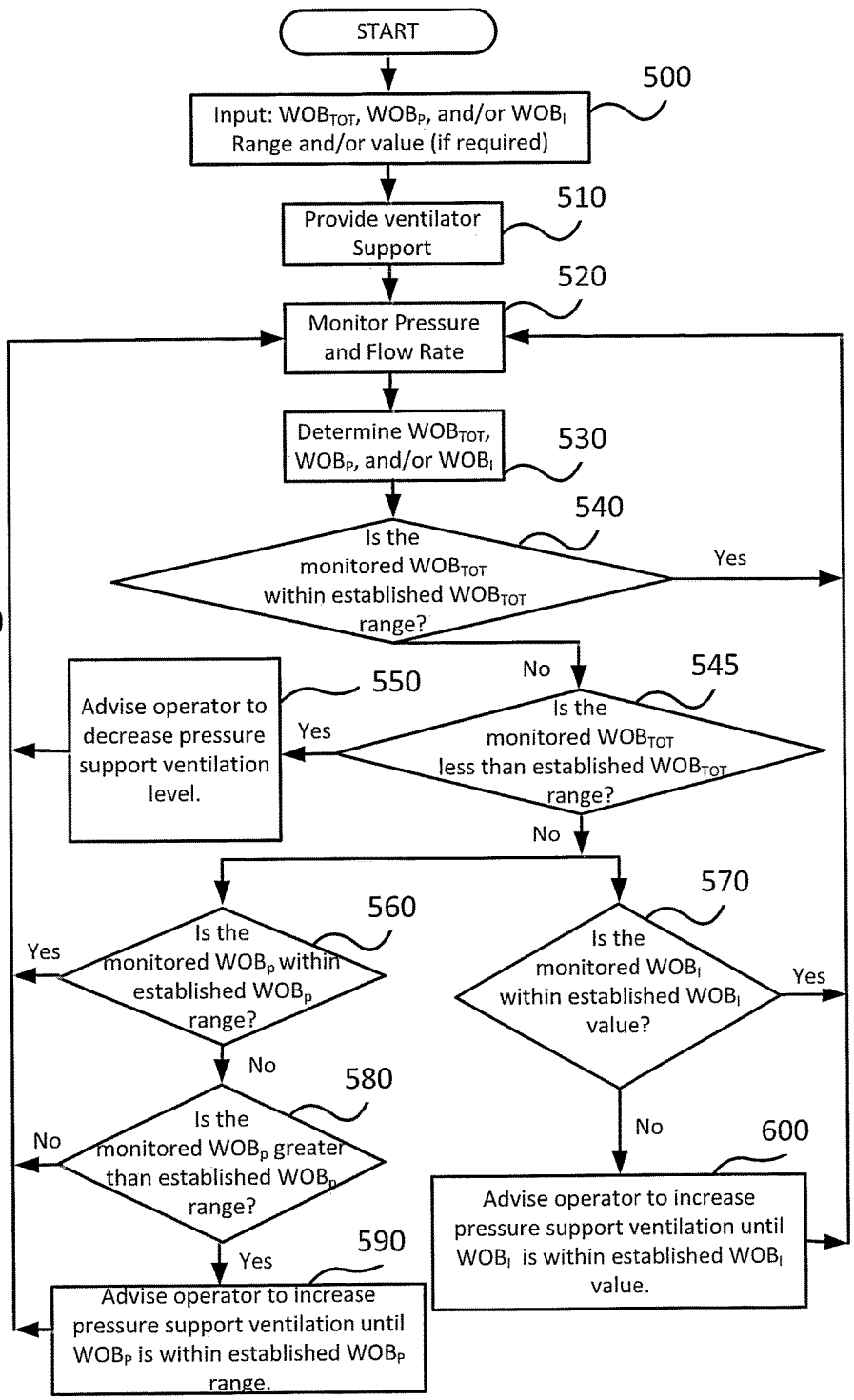
FIG. 10 is a flow chart illustrating a preferred sequence of steps for carrying out an open-loop operation for assessing work of breathing in accordance with the present invention.

FIG. 10 shows a flowchart for a preferred embodiment of the software that controls the open-loop operation. The program continues to execute as long as the ventilator 20 or processing system 60 is not reset. At step 500, the input parameters are selected, such as the desired or predetermined $WOB_{TOT}$, $WOB_P$ and/or $WOB_I$ range/value. In a preferred embodiment, the $WOB_{TOT}$ range is 5-10 J/min and the $WOB_I$ is zero. At step 510, the ventilator 20 supplies breathing gas 32 to the patient 10 via the ventilator conduit 40 at the selected pressure support ventilation level. At step 520, the airway flow, pressure and tracheal pressure is measured. At step 530, the $WOB_{TOT}$, $WOB_P$ and/or $WOB_I$ of the patient 10 is calculated from the sensed pressure, airway flow rate and tracheal pressure. In step 540, it is determined if the measured $WOB_{TOT}$ is within the predetermined $WOB_{TOT}$ range. If the $WOB_{TOT}$ is within the predetermined range, the processing system then steps back to block 520 to continuously monitor $WOB_{TOT}$, $WOB_P$ and/or $WOB_I$.

If measured $WOB_{TOT}$ is not within the predetermined $WOB_{TOT}$ range, then it is determined in step 545 if the measured $WOB_{TOT}$ is less than the predetermined $WOB_{TOT}$ range. If the $WOB_{TOT}$ is less than the predetermined $WOB_{TOT}$ range, then in step 550 the operator is advised (e.g. by visual display or user interface) of the monitored patient $WOB_{TOT}$ and is advised to decrease pressure support ventilation to the patient. In certain embodiments, the operator is advised to decrease pressure support ventilation in 2-5 cm/H$_2$O steps, and more preferably in 2 cm/H$_2$O steps, until the measured $WOB_{TOT}$ is within the established $WOB_{TOT}$ range.

If the $WOB_{TOT}$ is greater than the predetermined $WOB_{TOT}$ range, then in steps 560 and 570, it is determined if the measured $WOB_P$ is within the predetermined $WOB_P$ range and if the measured $WOB_I$ is greater than the established $WOB_I$ value, respectively. If the measured $WOB_P$ is within the predetermined range and the $WOB_I$ is within the established $WOB_I$ value, the processing system then steps back to Block 520 to continuously monitor $WOB_{TOT}$, $WOB_P$ and/or $WOB_I$.

If the measured $WOB_P$ is not within the established $WOB_P$ range, then it is determined in Block 580 whether $WOB_P$ is greater than the predetermined $WOB_P$ range. If the $WOB_P$ is not greater than the predetermined $WOB_P$ range, the processing system then steps back to Block 520 to continuously monitor $WOB_{TOT}$, $WOB_P$ and/or $WOB_I$. If the $WOB_P$ is greater than the predetermined $WOB_P$ range, in Block 590 the proposed action necessary to address increased monitored $WOB_P$ and treat the patient is displayed. Specifically, the operator is advised to increase pressure support ventilation. Preferably, the operator is advised to increase pressure support ventilation in about 2 cm/H$_2$O to 5 cm/H$_2$O steps until the measured patient $WOB_P$ is between about 5-10 J/min. Even more preferably the operator is advised to increase pressure support ventilation in 2 cm/H$_2$O steps until the monitored $WOB_P$ is between 5-10 J/min.

If the $WOB_I$ is greater than the established $WOB_I$ value, then in Block 600 the proposed action necessary to address increased measured patient $WOB_I$ and treat the patient is displayed. Specifically, the operator is advised to increase pressure support ventilation until monitored patient $WOB_I$ is within the established $WOB_I$ value. Preferably, the operator is advised to increase pressure support ventilation in about 2 cm/H$_2$O to 5 cm/H$_2$O steps until the monitored $WOB_I$ is at zero. Even more preferably the operator is advised to increase pressure support ventilation in 2 cm/H$_2$O steps until the monitored $WOB_P$ is at zero.

The ventilator 20 or processing system 60 may also alarm the operator that the patient's $WOB_P$ and/or $WOB_I$ are not within the desired $WOB_P$ and/or $WOB_I$ range/value. After displaying the proposed actions 590, 600, the processing system 60 steps back to step 520 to continuously monitor $WOB_{TOT}$, $WOB_P$ and/or $WOB_I$.

Figure 11:
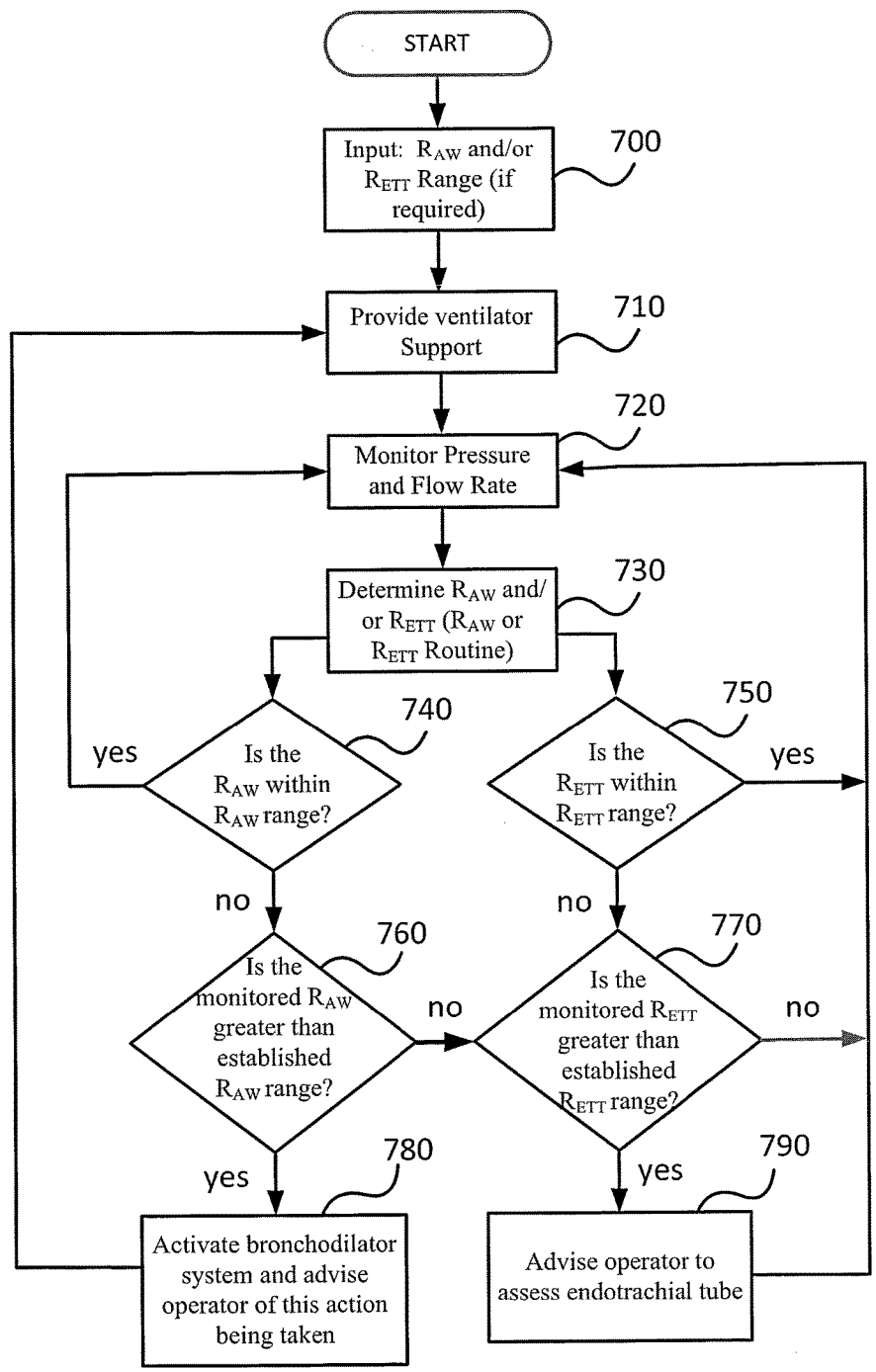
FIG. 11 is a flow chart illustrating a sequence of steps for carrying out an embodiment of a closed-loop operation of the present invention.

The closed-loop operation for delivery of bronchodilatory therapy is similar to the open-loop operation with the exception that the processing system 60 of the closed-loop operation automatically determines, sets, and delivers the bronchodilator therapy that will maintain the patient's $R_{AW}$ within the desired predetermined $R_{AW}$ range. Referring to FIG. 11, a general overview of the closed-loop operation is shown. Just as in the open-loop operation described above, the processing system is responsive to the airway flow, pressure and tracheal pressure signals to continuously determine the $R_{AW}$ and/or $R_{ETT}$ of the patient 10.

The processing system compares the monitored $R_{AW}$ and/or $R_{ETT}$ of the patient 10 to a predetermined $R_{AW}$ and/or $R_{ETT}$ range and generates a response signal based on the comparison when the patient's $R_{AW}$ and/or $R_{ETT}$ is not within the predetermined $R_{AW}$ and/or $R_{ETT}$. Then, in response to the response signal of the processing system, the alarm means may generate an alarm that is suitable for alerting an operator that the patient $R_{AW}$ and/or $R_{ETT}$ is not within the predetermined $R_{AW}$ and/or $R_{ETT}$ range and the regulating means of the processing system adjusts at least one of the actuators 86 of the bronchodilator system 80 (of the ventilator 20 if located therein). The actuator 86 is adjusted to administer a bronchodilator 82 to the patient 10. Thus, the regulating means, which is responsive to the response signal, regulates the bronchodilator provided to the patient by the bronchodilator system if the patient's $R_{AW}$ is greater than the predetermined $R_{AW}$. The administration of the bronchodilator continues until the monitored $R_{AW}$ falls back within the predetermined $R_{AW}$ range.

Thus, in the closed-loop operation, upon the input of the desired predetermined $R_{AW}$ range (and the predetermined $R_{ETT}$ range, if required) in Block 700, the ventilator 20 begins to provide ventilation, as shown in Block 710. The processing system, in Block 720, then monitors the airway pressure, flow and tracheal pressure of the patient 10 and, calculates $R_{AW}$ and/or $R_{ETT}$ of the patient in Block 730. Blocks 740 and 750 determine whether $R_{AW}$ and/or $R_{ETT}$ is or is not within the desired $R_{AW}$ and/or $R_{ETT}$ range. If the $R_{AW}$ and/or $R_{ETT}$ is within the predetermined range, the processing system then steps back to Block 720 to continuously monitor $R_{AW}$ and/or $R_{ETT}$. If the $R_{AW}$ and/or $R_{ETT}$ is not within the predetermined $R_{AW}$ and/or $R_{ETT}$, then it is determined in Blocks 760 and 770 whether $R_{AW}$ and/or $R_{ETT}$ is greater than the predetermined $R_{AW}$ and/or $R_{ETT}$.

If the $R_{AW}$ and/or $R_{ETT}$ is not greater than the predetermined $R_{AW}$ and/or $R_{ETT}$ range, the processing system then steps back to Block 720 to continuously monitor airway pressure and flow rate. If the $R_{AW}$ and/or $R_{ETT}$ is greater than the predetermined $R_{AW}$ and/or $R_{ETT}$ range, in Blocks 780 and 790 the actions necessary to address increased $R_{AW}$ and/or $R_{ETT}$ and treat the patient are taken.

For example, where the $R_{AW}$ is greater than the established range, in Block 780, the processing system automatically begins to deliver bronchodilator therapy to the patient and notifies the operator that bronchodilator therapy has been administered to the patient. No intermediate or intervening actions are required from the operator to administer the bronchodilator therapy. The closed-loop operation thereby provides for the automatic delivery of bronchodilator therapy in response to the changing status needs of the patient 10.

Where the $R_{ETT}$ is greater than the established range, in Block 790, the processing system automatically advises the operator to assess the patient's endotracheal tube.

The ventilator 20 or processing system 60 may also notify the operator that the patients monitored $R_{AW}$ and/or $R_{ETT}$ are not within the desired $R_{AW}$ and/or $R_{ETT}$ range. In addition, the ventilator 20 or processing system 60 may also advise the operator of the patient's $R_{AW}$ and/or $R_{ETT}$ monitored values.

Figure 12:
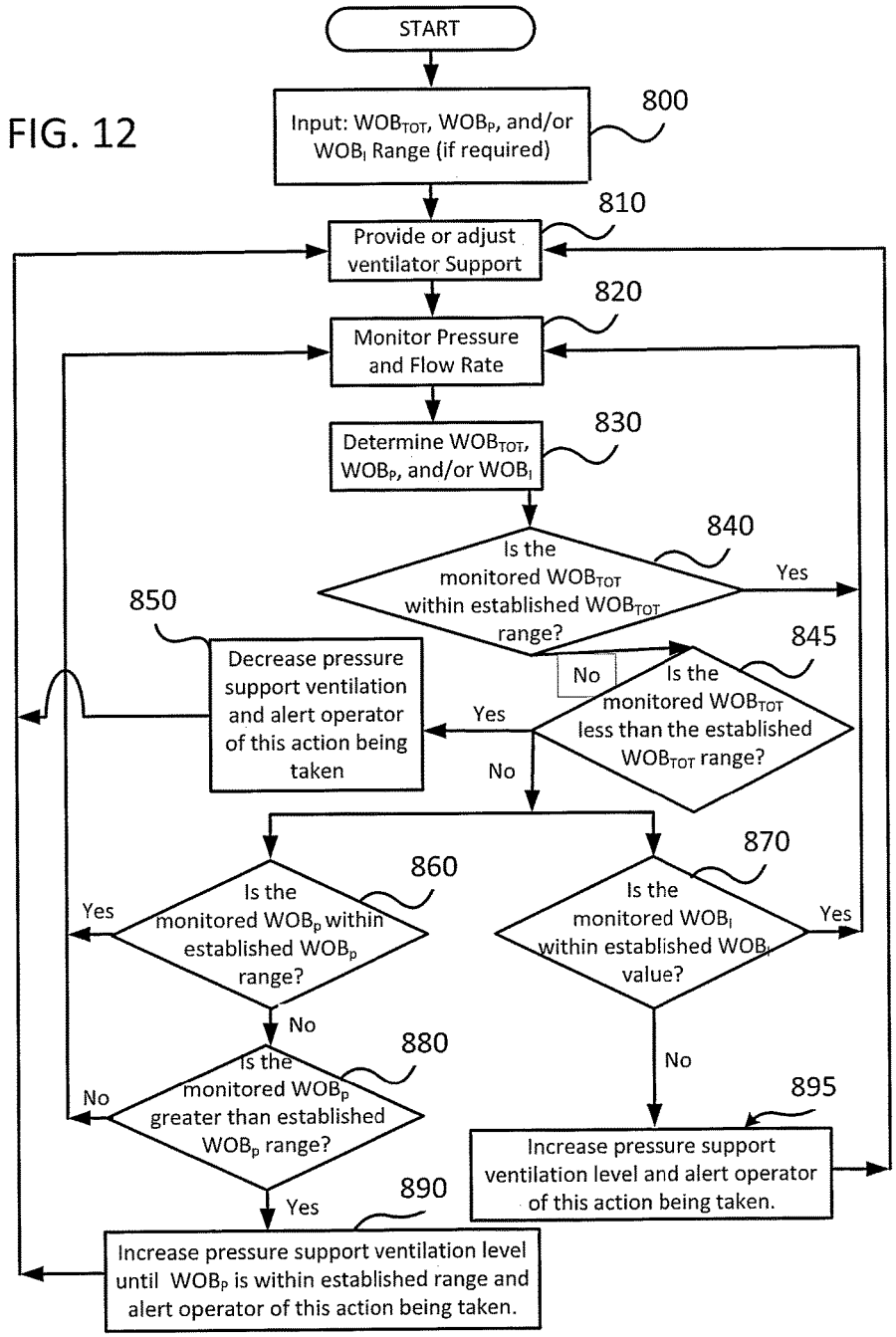
FIG. 12 is a flow chart illustrating a sequence of steps for carrying out another embodiment of a closed-loop operation of the present invention.

With the closed-loop operation for automated pressure support ventilation based on monitored $WOB_{TOT}$, $WOB_P$ and $WOB_I$, it is similar to the open-loop operation with the exception that the processing system 60 of the closed-loop operation automatically determines, sets, and delivers the appropriate pressure support ventilation therapy that will maintain the patient's $WOB_{TOT}$ within the desired predetermined $WOB_{TOT}$ range. Referring to FIG. 12, a general overview of the closed-loop operation is shown. Just as in the open-loop operation described above, the processing system is responsive to the airway flow, pressure and tracheal pressure signals to continuously determine the $WOB_{TOT}$, $WOB_P$ and/or $WOB_I$ of the patient 10.

The processing system compares the measured $WOB_{TOT}$, $WOB_P$ and/or $WOB_I$ of the patient 10 to a predetermined $WOB_{TOT}$, $WOB_P$ and/or $WOB_I$ range or value and generates a response signal based on the comparison when the patient's $WOB_{TOT}$, $WOB_P$ and/or $WOB_I$ is not within the predetermined $WOB_{TOT}$, $WOB_P$ and/or $WOB_I$ range or value. Then, in response to the response signal of the processing system, the alarm means may generate an alarm that is suitable for alerting an operator that the patient $WOB_{TOT}$, $WOB_P$ and/or $WOB_I$ is not within the predetermined $WOB_{TOT}$, $WOB_P$ and/or $WOB_I$ range and the regulating means of the processing system adjusts at least one of the actuators 28 of the pneumatic system 22 (of the ventilator 20 if located therein). The actuator(s) 28 is adjusted to administer appropriate pressure support ventilation to the patient 10. For example, a pressure support ventilation level may be altered by adjusting actuator(s) 28. Thus, the regulating means, which is responsive to the response signal, regulates the breathing gas provided to the patient by the ventilator if the patient's $WOB_{TOT}$ is greater than the predetermined $WOB_{TOT}$. The change in pressure support ventilation level is maintained until the monitored $WOB_{TOT}$, $WOB_P$ and/or $WOB_I$ falls back within the predetermined $WOB_{TOT}$, $WOB_P$ and/or $WOB_I$ range or value.

Thus, in the closed-loop operation, upon the input of the desired predetermined $WOB_{TOT}$ range (and the predetermined $WOB_P$ and/or $WOB_I$ range or value, if required) in Block 800, the ventilator 20 begins to provide pressure support ventilation, as shown in Block 810. The processing system, in Block 820, then monitors the airway pressure, flow and tracheal pressure of the patient 10 and, calculates $WOB_{TOT}$, $WOB_P$ and/or $WOB_I$ of the patient in Block 830. Block 840 determines whether $WOB_{TOT}$ is or is not within the established $WOB_{TOT}$ range. If the measured $WOB_{TOT}$ is within the predetermined range, then processing system then steps back to Block 820 to continuously monitor airway pressure airway pressure, flow and tracheal pressure.

If the measured $WOB_{TOT}$ is not within the predetermined range, then the processing system queries in Block 845 whether monitored patient $WOB_{TOT}$ is less than the predetermined range. If the monitored patient $WOB_{TOT}$ is less than the established $WOB_{TOT}$ range, the processing system then, as shown in Block 850 and 810, automatically begins to provide appropriate ventilator support (e.g., decrease pressure support ventilation level). Specifically, the processing system automatically decreases the pressure support ventilation level in about 2 cm/H$_2$O to 5 cm/H$_2$O steps until the monitored patient $WOB_{TOT}$ is within the established $WOB_{TOT}$ range. Preferably, the processing system automatically decreases the pressure support ventilation level in about 2 cm/H$_2$O steps until the monitored patient $WOB_{TOT}$ is within the range of 5-10 J/min. No intermediate or intervening actions are required from the operator to administer the pressure support ventilation therapy.

If the monitored patient $WOB_{TOT}$ is greater than the predetermined $WOB_{TOT}$ range, then the processing system queries whether monitored patient $WOB_P$ and/or $WOB_I$ are within the established $WOB_P$ and/or $WOB_I$ range or value, Blocks 860 and 870, respectively. If the $WOB_P$ and/or $WOB_I$ is within the predetermined range or value, the processing system then steps back to Block 820 to continuously monitor pressure and flow rates.

If the measured patient $WOB_P$ is not within the predetermined $WOB_P$ range, then it is determined in Block 880 whether monitored patient $WOB_P$ is greater than the predetermined $WOB_P$ range. If the measured patient $WOB_P$ is not greater than the predetermined $WOB_P$ range, the processing system then steps back to Block 820 to continuously monitor pressure and flow rate.

If the monitored patient $WOB_P$ is greater than the predetermined $WOB_P$ range, in Block 890 and 810, the processing system then automatically begins to provide appropriate ventilator support to treat the patient. Specifically, the processing system will increase the pressure support ventilation level in about 2 cm/H$_2$O to 5 cm/H$_2$O steps until the measured patient $WOB_P$ is within 5-10 J/min. Preferably, the pressure support ventilation level is adjusted in 2 cm/H$_2$O steps. No intermediate or intervening actions are required from the operator to administer pressure support ventilator therapy. Rather, the operator may be alerted that an amended pressure support ventilation level has been administered to the patient (e.g., via alarm and/or display).

If the monitored patient $WOB_I$ is greater than the predetermined $WOB_I$ value, then the processing system in Blocks 900 and 810 automatically begins to provide actions necessary to address the increased measured patient $WOB_I$ and to treat the patient. Specifically, the processing system will increase the pressure support ventilation level in about 2 cm/H$_2$O to 5 cm/H$_2$O steps until the $WOB_I$ is measured at zero. No intermediate or intervening actions are required from the operator to administer pressure support ventilator therapy. Rather, the ventilator 20 or processing system 60 may transmit an alarm and/or display to the operator that the patient's $WOB_I$ is greater than zero and that action is being taken to increase the pressure support ventilation level.

In a preferred embodiment, the system first ascertains whether $WOB_I$ is greater than zero and automatically administers pressure support ventilator therapy as necessary so that $WOB_I$ is at zero before ascertaining whether $WOB_P$ is within the established range. Once $WOB_I$ is at zero, then the measured patient $WOB_P$ is assessed to determine whether it is within the established range of 5-10 J/min. If $WOB_P$ is greater than the established range, preferably, the pressure support ventilation level is adjusted in 2 cm/H$_2$O steps. No intermediate or intervening actions are required from the operator to administer pressure support ventilator therapy. Rather, the ventilator 20 or processing system 60 may transmit an alarm and/or display to the operator that the patient's $WOB_I$ is at zero and that $WOB_P$ is greater than the desired $WOB_P$ range and that action is being taken to increase the pressure support ventilation level. The closed-loop operation thereby provides for the automatic delivery of pressure support ventilation in response to the changing status needs of the patient 10.

Description of Neural Networks

Artificial neural networks loosely model the functioning of a biological neural network, such as the human brain. Accordingly, neural networks are typically implemented as computer simulations of a system of interconnected neurons. In particular, neural networks are hierarchical collections of interconnected processing elements (PEs). These elements are typically arranged in layers, where the input layer receives the input data, the hidden layers transform the data, and the output layer produces the desired output. Other embodiments of a neural network can also be used.

Each processing element in the neural network receives multiple input signals, or data values, that are processed to compute a single output. The inputs are received from the outputs of PEs in the previous layer or from the input data. The output value of a PE is calculated using a mathematical equation, known in the art as an activation function or a transfer function that specifies the relationship between input data values. As known in the art, the activation function may include a threshold, or a bias element. The outputs of elements at lower network levels are provided as inputs to elements at higher levels. The highest level element, or elements, produces a final system output, or outputs.

Figure 13:
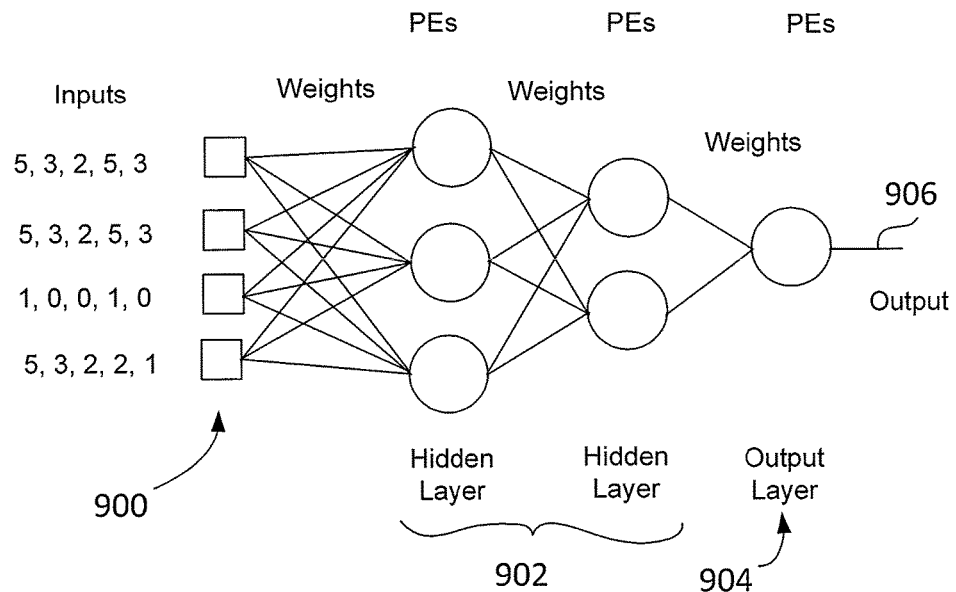
FIG. 13 depicts a neural network showing hidden layers.

In the context of the present invention, the neural network is a computer simulation that is used to produce a noninvasive estimate of the quantified patient physiologic airway resistance and physiologic work of breathing described previously. The neural network of the present invention may be constructed by specifying the number, arrangement, and connection of the processing elements which make up the network. A simple embodiment of a neural network consists of a fully connected network of processing elements. As shown in FIG. 13, the processing elements of the neural network are grouped into the following layers: an input layer 900 where the parameters collected and/or derived from the airway pressure and flow sensors are inputted to the network; a hidden layer or layers 902 of processing elements; and an output layer 904 where the resulting prediction of patient effort 906 is produced. The number of connections, and consequently the number of connection weights, is fixed by the number of elements in each layer 900, 902, 904.

Figure 14:
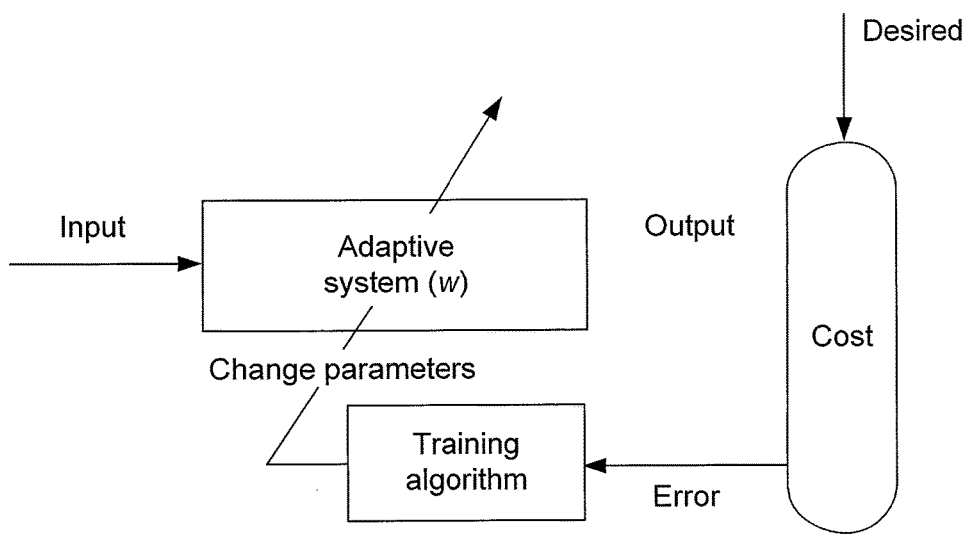
FIG. 14 depicts inputs and outputs of an adaptive system having back-propagation.

The most common training methodology for neural networks is based upon iterative improvement of the system parameters (normally called weights) by minimizing the mean squared difference between the desired output and the network output (mean squared error, MSE). The input is applied to the neural network, the neural network passes the data through its hierarchical structure, and an output is created. This network output is compared with the desired output corresponding to that input and an error is calculated. This error is then used to adjust the weights of the system so that the next time that particular input is applied to the system the network output will be closer to the desired output. There are many possible methodologies to adjust the weights, called the training algorithm. As shown in FIG. 14, the most common is called backpropagation that involves calculating each weight's responsibility for the error, and calculating a local gradient from this error in order to use a gradient descent learning rule for each weight.

As one skilled in the art will appreciate, embodiments of the present invention may be embodied as, among other things: a method, system, or computer-program product. Accordingly, the embodiments may take the form of a hardware embodiment, a software embodiment, or an embodiment combining software and hardware. In one embodiment, the present invention takes the form of a computer-program product that includes computer-useable instructions for monitoring $R_{AW}$, $R_{ETT}$, $R_{TOT}$, $WOB_I$, $WOB_P$, and $WOB_{TOT}$, embodied on one or more computer-readable media.

As a computer readable medium containing program instructions, an embodiment of the invention includes: computer readable code devices for receiving input variables, processing the input, and providing an output indicative of $R_{AW}$, $R_{ETT}$, $R_{TOT}$, $WOB_I$, $WOB_P$, and $WOB_{TOT}$. In a preferred embodiment, processing comprises utilizing a neural network. The method may further include controlling a ventilator and/or bronchodilator delivery system in response to the output (monitored $R_{AW}$, $R_{ETT}$, $R_{TOT}$, $WOB_I$, $WOB_P$, and $WOB_{TOT}$) obtained.

Computer-readable media include both volatile and nonvolatile media, removable and nonremovable media, and contemplate media readable by a database, a switch, and various other network devices. By way of example, and not limitation, computer-readable media comprise media implemented in any method or technology for storing information. Examples of stored information include computer-useable instructions, data structures, program modules, and other data representations. Media examples include, but are not limited to, information-delivery media, RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data momentarily, temporarily, or permanently.

The invention may be practiced in distributed-computing environments where tasks are performed by remote-processing devices that are linked through a communications network. In a distributed-computing environment, program modules may be located in both local and remote computer-storage media including memory storage devices. The computer-useable instructions form an interface to allow a computer to react according to a source of input. The instructions cooperate with other code segments to initiate a variety of tasks in response to data received in conjunction with the source of the received data.

The present invention may be practiced in a network environment such as a communications network. Such networks are widely used to connect various types of network elements, such as routers, servers, gateways, and so forth. Further, the invention may be practiced in a multi-network environment having various, connected public and/or private networks.

Communication between network elements may be wireless or wireline (wired). As will be appreciated by those skilled in the art, communication networks may take several different forms and may use several different communication protocols. And the present invention is not limited by the forms and communication protocols described herein. One skilled in the art of computer science will easily be able to combine the software created as described with appropriate general purpose or special purpose computer hardware to create a computer system or computer sub-system embodying the method of the invention. An apparatus for making, using or selling the invention may be one or more processing systems including, but not limited to, a central processing unit (CPU), memory, storage devices, communication links and devices, servers, I/O devices, or any sub-components of one or more processing systems, including software, firmware, hardware or any combination or subset thereof, which embody the invention. User input may be received from the keyboard, mouse, pen, voice, touch screen, or any other means by which a human can input data into a computer, including through other programs such as application programs.

Example 1

Figure 15:
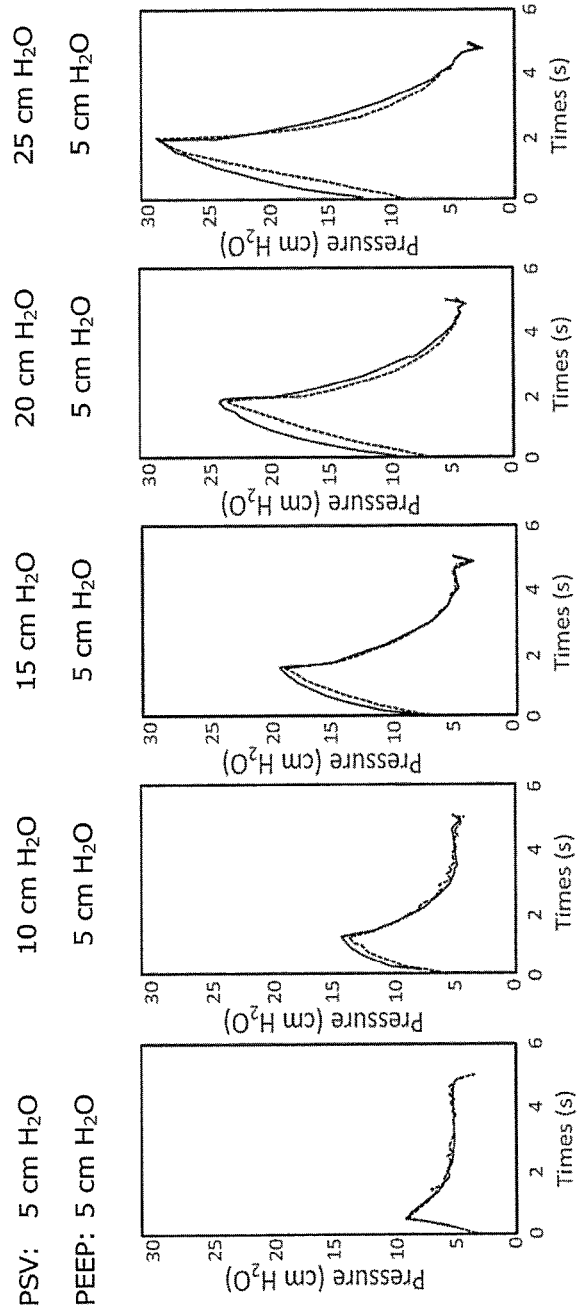
FIG. 15 shows simultaneous measurements of tracheal airway pressure during inhalation and exhalation at various levels of pressure support ventilation (PSV) at the same level of positive end expiratory pressure (PEEP) measured by two methods, (1) from a catheter inserted inside and positioned at the distal end of an endotracheal tube and (2) estimated from the endotracheal tube cuff derived in accordance with the methods disclosed herein.

A patient was observed in the hospital setting with varying levels of pressure support ventilation (PSV) to determine if the algorithms as described herein using the endotracheal tube cuff can estimate the pressure at the distal end of the endotracheal tube (tracheal airway pressure). The control pressure was determined by inserting a catheter to the distal end of the endotracheal tube. The experimental pressure was estimated by monitoring the pressure inside the cuff of the endotracheal tube. The PEEP level was set at 5 cm $H_2O$. The PSV levels were 5, 10, 15, 20, and 25 cm $H_2O$. The algorithm using endotracheal tube cuff pressure was found to have high agreement with the tracheal airway pressure. FIG. 15 illustrates the results from the study, where the estimated tracheal pressure using the endotracheal tube cuff ($P_{Trach\ Est}$) was in agreement with actual tracheal pressure as measured using the catheter ($P_{Trach}$).

Example 2

A patient treated with minimum ventilator settings (e.g., PEEP level set at 5 cm H2O, PSV level set at 5 cm $H_2O$, and $FIO_2$ at 0.3) can be assessed using the methods described herein to determine whether to wean and/or extubate the patient. As discussed above, current conventional methods only assess $WOB_{TOT}$ to determine patient status. However, determination of only $WOB_{TOT}$ does not enable the clinician to accurately assess whether a patient may be extubated or whether pressure support ventilation therapy should be amended.

Either an open or closed-loop system or operation for automated pressure support ventilation based on monitored $WOB_{TOT}$, $WOB_P$ and $WOB_I$ can be applied to a patient being treated with minimum ventilator settings. With such patients, in either the open-loop or closed-loop operation, the processing system 60 automatically determines whether the patient should be weaned and/or extubated from pressure support ventilation therapy.

Initially, desired predetermined $WOB_{TOT}$ range (and the predetermined $WOB_P$ and/or $WOB_I$ range or value, if required) is input into the system or operation. The ventilator 20 begins to provide pressure support ventilation with minimum ventilator settings. The processing system then monitors the airway pressure, flow and tracheal pressure of the patient 10 and, calculates $WOB_{TOT}$, $WOB_P$ and/or $WOB_I$ of the patient. The processing system determines whether $WOB_{TOT}$ is or is not within the established $WOB_{TOT}$ range. If the measured $WOB_{TOT}$ is within the predetermined range, the processing system then returns to continuously monitoring airway pressure, airway flow pressure and tracheal pressure.

If the measured $WOB_{TOT}$ is not within the predetermined range, then the processing system queries whether monitored patient $WOB_{TOT}$ is less than the predetermined range. If the monitored patient $WOB_{TOT}$ is less than the established $WOB_{TOT}$ range, the processing system in an open loop system (or operation) would notify the clinician that $WOB_{TOT}$ is below the predetermined range and provide a recommendation for further action. In a preferred embodiment, the processing system would notify the clinician to extubate and/or wean the patient.

In a closed loop system (operation), when the processing system establishes that monitored patient $WOB_{TOT}$ is less than the established $WOB_{TOT}$ range, the processing system automatically begins to provide appropriate ventilator support (e.g., decrease pressure support ventilation level). Specifically, the processing system automatically decreases the pressure support ventilation level in about 2 cm/$H_2O$ to 5 cm/$H_2O$ steps until the monitored patient $WOB_{TOT}$ is within the established $WOB_{TOT}$ range. Preferably, the processing system automatically decreases the pressure support ventilation level in about 2 cm/$H_2O$ steps until the monitored patient $WOB_{TOT}$ is within the range of 5-10 J/min. No intermediate or intervening actions are required from the operator to administer the pressure support ventilation therapy. Rather, because the system is already set at minimum ventilator settings, the system may alert the clinician to extubate or wean the patient from ventilatory support.

If the monitored patient $WOB_{TOT}$ is greater than the predetermined $WOB_{TOT}$ range, then the processing system queries whether monitored patient $WOB_P$ is within or below the established $WOB_P$ range. Preferably, the established $WOB_P$ range is at about 5-10 J/min. If the $WOB_P$ is within the established range (e.g., if the patient's $WOB_P$ is at 5 J/min.; thus establishing that most of increase in $WOB_{TOT}$ is due to imposed work of breathing), in an open or closed loop system, the processing system will provide a recommendation to extubate or wean the patient.

If the measured patient $WOB_P$ is greater than the established $WOB_P$ range, in an open loop system (or operation), the processing system will provide notification that $WOB_P$ is greater than zero and may provide information regarding appropriate ventilator support needed to treat the patient.

Alternatively, in a closed loop system, the processing system (upon establishing that the measured patient $WOB_P$ is greater than the established range) will then automatically begin to provide appropriate ventilator support to treat the patient. Specifically, the processing system will increase the pressure support ventilation level in about 2 cm/$H_2O$ to 5 cm/$H_2O$ steps until the measured patient $WOB_P$ is within the established $WOB_P$ range. Preferably, the pressure support ventilation level is adjusted in 2 cm/$H_2O$ steps. No intermediate or intervening actions are required from the operator to administer pressure support ventilator therapy. Rather, the operator may be alerted that an amended pressure support ventilation level has been administered to the patient (e.g., via alarm and/or display).

Once $WOB_P$ is within the established range, then the processing system will determine whether monitored patient $WOB_I$ is outside of the predetermined $WOB_I$ value of zero. If monitored patient $WOB_I$ is outside of the predetermined $WOB_I$ value, in an open or closed loop system, the processing system will provide a recommendation to proceed with weaning and/or extubating the patient.

Historically, using only patient monitored $WOB_{TOT}$, the clinician could not accurately determine an appropriate time to wean and/or extubate a patient, oftentimes weaning or extubating a patient later than when appropriate. With the systems and methods described herein, the clinician can accurately estimate $WOB_I$ and $WOB_P$ to determine when a patient is physically ready to be weaned or extubated from ventilation.

Endotracheal intubation and mechanical ventilation are a major risk factor for nosocomial infections, particularly ventilator-associated pneumonia (VAP). By enabling the clinician to accurately determine when a patient should be weaned and/or extubated, the subject invention is particularly useful in decreasing a patient's risk of developing a nosocomial infection. Furthermore, by decreasing time of treatment and perhaps even patient stay, the subject invention may assist in providing considerable savings in health care costs.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method comprising:
   (a) non-invasively measuring pressure and flow data from a breathing circuit of an intubated patient;
   (b) using the pressure and flow data from step (a), determining endotracheal pressure without an end-inspiratory pause and an end-expiratory pause; and
   (c) using the endotracheal pressure determined from step (b), calculating estimated real-time airway resistance ($R_{AW}$), endotracheal tube resistance ($R_{ETT}$), and total resistance ($R_{TOT}$) values, wherein the estimated $R_{AW}$ value is calculated based on the estimated $R_{ETT}$ and $R_{TOT}$ values, and wherein the pressure and flow data include pressure measured at a wye-piece of the breathing circuit, pressure measured at a distal end of an endotracheal tube, and airway flow within the breathing circuit, wherein the $R_{ETT}$ value is calculated based on a difference in tracheal airway pressure and pressure measured at the wye-piece, and dividing the difference by flow rate;
   determining whether the estimated $R_{AW}$ value or the estimated $R_{ETT}$ value is outside a predetermined $R_{AW}$ range or $R_{ETT}$ range, respectively; and
   determining based upon the determination of whether the estimated $R_{AW}$ value or the estimated $R_{ETT}$ value is outside the predetermined $R_{AW}$ range or the predetermined $R_{ETT}$ range, respectively i) whether to administer bronchodilator therapy, ii) whether the endotracheal tube is obstructed, iii) whether to titrate bronchodilator treatment, (iv) how to titrate bronchodilator treatment, v) whether to titrate ventilatory support, or vi) how to titrate ventilator support.

2. The method of claim 1, wherein the pressure measurement at the distal end of the endotracheal tube is performed using an endotracheal pressure cuff.

3. The method of claim 1, wherein step (c) includes estimating the patient expiratory time constant ($\tau_E$) to calculate estimated real-time $R_{AW}$, $R_{ETT}$, and $R_{TOT}$ values.

4. The method of claim 1, wherein the patient is on assisted or spontaneous ventilation.

5. The method of claim 1, further comprising calculating physiologic tracheal pressure $P_{trach}$ and estimating a patient expiratory time constant ($\tau_E$), based on the physiologic tracheal pressure $P_{trach}$, prior to calculating estimated real-time airway resistance ($R_{AW}$), endotracheal tube resistance ($R_{ETT}$), and total resistance ($R_{TOT}$) values.

6. The method of claim 1, wherein breathing gas from a ventilator is supplied to and from the patient via a ventilator flow conduit having the endotracheal tube in fluid communication with the patient, wherein the conduit and the endotracheal tube include sensors, wherein the ventilator has a display and at least one setting control for controlling the breathing gas supplied to and from the patient, and wherein determining whether to administer the bronchodilator therapy to a patient on ventilator support further comprises:
   (a) sensing the pressure of the breathing gas within the ventilator conduit and generating a pressure signal representative of that pressure;
   (b) measuring the flow rate of the breathing gas within the ventilator conduit and generating a flow signal representative of that flow rate;
   (c) measuring the pressure at the endotracheal tube and generating an intra-tracheal pressure signal representative of that pressure; and
   (d) processing the pressure, flow rate and intra-tracheal pressure signal to determine the estimated $R_{AW}$ value.

7. The method of claim 1, further comprising:
   causing display of a recommendation i) whether to administer the bronchodilator therapy based upon the estimated $R_{AW}$ value being outside of the predetermined $R_{AW}$ range, ii) whether to check the endotracheal tube based upon the estimated $R_{ETT}$ value being outside of the predetermined $R_{ETT}$ range, iii) whether to titrate bronchodilator treatment, (iv) how to titrate bronchodilator treatment, v) whether to titrate ventilatory support, or vi) how to titrate ventilator support.

8. The method of claim 1, further comprising:
   providing a visual or audio alarm in response to i) determining that the bronchodilator therapy is to be administered, ii) that the endotracheal tube is obstructed, iii) determining to titrate bronchodilator treatment, (iv) how to titrate bronchodilator treatment, v) determining to titrate ventilatory support, or vi) how to titrate ventilator support.

9. The method of claim 1, wherein breathing gas from a ventilator is supplied to and from the patient via a ventilator flow conduit having the endotracheal tube in fluid communication with the patient, wherein the conduit and the endotracheal tube include sensors, wherein the ventilator has a display and at least one setting control for controlling the breathing gas supplied to and from the patient, and wherein determining whether the endotracheal tube of an intubated patient on ventilator support is obstructed further comprises:
   (a) sensing the pressure of the breathing gas within the ventilator conduit and generating a pressure signal representative of that pressure;
   (b) measuring the flow rate of the breathing gas within the ventilator conduit and generating a flow signal representative of that flow rate;
   (c) measuring the pressure at the endotracheal tube and generating an intra-tracheal pressure signal representative of that pressure; and
   (d) processing the pressure, flow and intra-tracheal pressure signal to determine the estimated $R_{ETT}$ value.

10. A system comprising:
    a ventilator conduit having an endotracheal tube, wherein the conduit and the endotracheal tube include sensors;
    a user interface, one or more processors, and one or more non-transitory computer-readable media having computer-useable instructions embodied thereon that, when executed, causes the one or more processors of the system to:
    (a) non-invasively measuring pressure and flow data from a breathing circuit of an intubated patient;

(b) using the pressure and flow data from step (a), determining endotracheal pressure without an end-inspiratory pause and an end-expiratory pause; and
(c) using the endotracheal pressure determined from step (b), calculating estimated real-time airway resistance ($R_{AW}$), endotracheal tube resistance ($R_{ETT}$), and total resistance ($R_{TOT}$) values, wherein the estimated $R_{AW}$ value is calculated based on the estimated $R_{ETT}$ and $R_{TOT}$ values, and wherein the pressure and flow data include pressure measured at a wye-piece of the breathing circuit, pressure measured at a distal end of the endotracheal tube, and airway flow within the breathing circuit, wherein the $R_{ETT}$ value is calculated based on a difference in tracheal airway pressure and pressure measured at the wye-piece, and dividing the difference by flow rate;
determine whether the estimated $R_{AW}$ value or the estimated $R_{ETT}$ value is outside a $R_{AW}$ range or $R_{ETT}$ range, respectively; and
determine based upon the determination of whether the estimated $R_{AW}$ value or the estimated $R_{ETT}$ value is outside the predetermined $R_{AW}$ range or the $R_{ETT}$ range, respectively i) whether to administer bronchodilator therapy, ii) whether the endotracheal tube is obstructed, iii) whether to titrate bronchodilator treatment, (iv) how to titrate bronchodilator treatment, v) whether to titrate ventilatory support, or vi) how to titrate ventilator support.

11. The system of claim 10, wherein the pressure measurement at the distal end of the endotracheal tube is performed using an endotracheal pressure cuff.

12. The system of claim 10, wherein step (c) includes estimating the patient expiratory time constant ($\tau_E$) to calculate estimated real-time $R_{AW}$, $R_{ETT}$, and $R_{TOT}$ values.

13. The system of claim 10, wherein the patient is on assisted or spontaneous ventilation.

14. The system of claim 10, wherein the one or more non-transitory computer-readable media having computer-useable instructions further causes the one or more processors to:
calculate physiologic tracheal pressure $P_{trach}$ and estimate a patient expiratory time constant ($\tau_E$), based on the physiologic tracheal pressure $P_{trach}$, prior to calculating the estimated real-time airway resistance ($R_{AW}$), endotracheal tube resistance ($R_{ETT}$), and total resistance ($R_{TOT}$) values.

15. The system of claim 10, wherein breathing gas from the ventilator is supplied to and from the patient via a ventilator flow conduit having the endotracheal tube attachment in fluid communication with the patient, wherein the conduit and the endotracheal tube include the sensors, and wherein the ventilator has a display and at least one setting control for controlling the breathing gas supplied to and from the patient, and wherein determining whether to administer the bronchodilator therapy to a patient on ventilator support, further causes the one or more processors to:
(a) sense the pressure of the breathing gas within the ventilator conduit and generating a pressure signal representative of that pressure;
(b) measure the flow rate of the breathing gas within the ventilator conduit and generating a flow signal representative of that flow rate;
(c) measure the pressure at the endotracheal tube and generating an intra-tracheal pressure signal representative of that pressure; and
(d) process the pressure, flow rate and intra-tracheal pressure signal to determine the estimated $R_{AW}$ value.

16. The system of claim 10, wherein the one or more non-transitory computer-readable media having computer-useable instructions further causes the one or more processors to:
display a recommendation i) whether to administer the bronchodilator therapy based upon the estimated $R_{AW}$ being outside of the predetermined $R_{AW}$ range, ii) whether to check the endotracheal tube based upon the estimated $R_{ETT}$ value being outside of the predetermined $R_{ETT}$ range, iii) whether to titrate bronchodilator treatment, (iv) how to titrate bronchodilator treatment, v) whether to titrate ventilatory support, or vi) how to titrate ventilator support.

17. The system of claim 10, wherein the one or more non-transitory computer-readable media having computer-useable instructions further causes the one or more processors to:
provide a visual or audio alarm in response to i) determining that the bronchodilator therapy is to be administered, ii) that the endotracheal tube is obstructed, iii) determining to titrate bronchodilator treatment, (iv) how to titrate bronchodilator treatment, v) determining to titrate ventilatory support, or vi) how to titrate ventilator support.

18. The system of claim 10, wherein breathing gas from a ventilator is supplied to and from the patient via a ventilator flow conduit having the endotracheal tube in fluid communication with the patient, wherein the conduit and the endotracheal tube include sensors, and wherein the ventilator has a display and at least one setting control for controlling the breathing gas supplied to and from the patient, and wherein determining whether the endotracheal tube of an intubated patient on ventilator support is obstructed further causes the one or more processors to:
(a) sense the pressure of the breathing gas within the ventilator conduit and generating a pressure signal representative of that pressure;
(b) measure the flow rate of the breathing gas within the ventilator conduit and generating a flow signal representative of that flow rate;
(c) measure the pressure at the endotracheal tube and generating an intra-tracheal pressure signal representative of that pressure; and
(d) process the pressure, flow and intra-tracheal pressure signal to determine the estimated $R_{ETT}$ value.

19. A computer program product comprising one or more non-transitory computer-readable media having computer-readable code stored therein, the computer-readable code comprising computer-useable instructions for:
(a) non-invasively measuring pressure and flow data from a breathing circuit of an intubated patient;
(b) using the pressure and flow data from step (a), determining endotracheal pressure without an end-inspiratory pause and an end-expiratory pause; and
(c) using the endotracheal pressure determined from step (b), calculating estimated real-time airway resistance ($R_{AW}$), endotracheal tube resistance ($R_{ETT}$), and total resistance ($R_{TOT}$) values, wherein the estimated $R_{AW}$ value is calculated based on the estimated $R_{ETT}$ and $R_{TOT}$ values, and wherein the pressure and flow data include pressure measured at a wye-piece of the breathing circuit, pressure measured at a distal end of an endotracheal tube, and airway flow within the breathing circuit, wherein the $R_{ETT}$ value is calculated based on a difference in tracheal airway pressure and pressure measured at the wye-piece, and dividing the difference by flow rate;

determining whether the estimated $R_{AW}$ value or the estimated $R_{ETT}$ value is outside a predetermined $R_{AW}$ range or $R_{ETT}$ range, respectively; and determining based upon the determination of whether the estimated $R_{AW}$ value or the estimated $R_{ETT}$ value is outside the predetermined $R_{AW}$ range or the predetermined $R_{ETT}$ range, respectively i) whether to administer bronchodilator therapy, ii) whether the endotracheal tube is obstructed, iii) whether to titrate bronchodilator treatment, (iv) how to titrate bronchodilator treatment, v) whether to titrate ventilatory support, or vi) how to titrate ventilator support.

20. The computer program product of claim 19, wherein the pressure measurement at the distal end of the endotracheal tube is performed using an endotracheal pressure cuff.

\* \* \* \* \*